United States Patent [19]

Fischer et al.

[11] Patent Number: 6,086,871
[45] Date of Patent: Jul. 11, 2000

[54] PROTHROMBIN DERIVATIVES

[75] Inventors: Bernhard Fischer, Vienna; Uwe Schlokat, Orth/Donau; Artur Mitterer, Orth/Donau; Falko-Günter Falkner, Orth/Donau; Johann Eibl, Vienna, all of Austria

[73] Assignee: Baxter Aktiengesellschaft, Vienna, Austria

[21] Appl. No.: 08/952,967

[22] PCT Filed: Jun. 12, 1996

[86] PCT No.: PCT/AT96/00105

§ 371 Date: Jan. 26, 1998

§ 102(e) Date: Jan. 26, 1998

[87] PCT Pub. No.: WO96/41868

PCT Pub. Date: Dec. 27, 1996

[30] Foreign Application Priority Data

Jun. 13, 1995 [AT]  Austria .................................... 1005/95

[51] Int. Cl.[7] .......................... A61K 38/48; C12P 21/04; C12N 1/20; C12N 15/00

[52] U.S. Cl. .................. 424/94.64; 435/69.6; 435/252.3; 435/320.1; 435/440; 536/23.2; 530/381; 530/384; 424/530

[58] Field of Search ..................... 435/69.6, 440, 435/252.3, 320.1; 536/23.1, 23.2; 530/381, 384; 424/94.64, 530

[56] References Cited

FOREIGN PATENT DOCUMENTS

| 0357242B1 | 3/1990 | European Pat. Off. . |
|---|---|---|
| 0367489A2 | 5/1990 | European Pat. Off. . |
| 0380443A3 | 8/1990 | European Pat. Off. . |
| 0714987A3 | 6/1996 | European Pat. Off. . |
| WO91/11519 | 8/1991 | WIPO . |
| WO92/057748 | 4/1992 | WIPO . |
| WO92/14750 | 9/1992 | WIPO . |
| WO93/15757 | 8/1993 | WIPO . |
| WO95/13385 | 5/1995 | WIPO . |

OTHER PUBLICATIONS

Bode et al. The Embo Jounal 8(11):3467–3475 (1989).
Bradford Analytical Biochemistry 72: 248–254 (1976).
Bruggener et al. Pharmazie 44: 648–649 (1989).
Degen et al. Biochemistry 26(19): 6165–6177 (1987).
Doyle et al. Methods In Enzymology 222: 299–312 (1993).
Fareed et al. Seminars In Thrombosis And Hemostasis 17(2): 137–144 (1991).
Fareed et al. The Faseb Journal 3(3), Abstract 592 (1989).
Fenton et al. Blood Coagulation And Fibrinolysis 2: 69–75 (1991).
Fischer et al. Journal of Biotechnology 38: 129–136 (1995).
Fischer et al. Febs Letters 351:345–348 (1994).
Gan et al. Archives Of Biochemistry And Biophysics 301(2): 228–236 (1993).
Graham et al. Virology 52: 456–467 (1973).
Grütter et al. The Embo Journal 9(8): 2361–2365 (1990).
Karshikov et al. Protein Science 727–735 (1992).
Klöcking et al. Blut 60: 129, Abstract 95 (1990).
Laemmli, Nature 227: 680–685 (1970).
Loison et al. Bio/Technology 6:72–77 (1988).
Macgregor et al. Nucleic Acids Research 17(6): 2365 (1989).
Markwardt et al. Pharmazie 43: 202–207 (1988).
Markwardt, Haemostasis 21(Suppl I): 11–26 (1991).
Markwardt, Thrombosis And Haemostasis 66(1): 141–152 (1991).
Mille et al. Clin. Chem 40(5): 734–739 (1994).
Pei et al. The Journal of Biological Chemistry 266(15): 9598–9604 (1991).
Quick, J. Biol. Chem. 109: 73–74 (1935).
Rigel et al. Circulation Research 72(5): 1091–1102 (1993).
Rydel et al. Science 249: 277–280 (1990).
Szyperski et al. J. Mol. Biol. 228: 1206–1211 (1992).
Urlaub et al. Proc Natl. Acad. Sci. USA 77(7): 4216–4220 (1980).
Walenga et al. Seminars In Thrombosis And Hemostasis 15(3): 316–333 (1989).
Wu et al. Proc Natl. Acad. Sci. USA 88: 6775–6779 (1991).
Zawilska et al. Thrombosis Research 69: 315–320 (1993).

*Primary Examiner*—Rebecca E. Prouty
*Assistant Examiner*—Tekchand Saidha
*Attorney, Agent, or Firm*—Foley & Lardner

[57] ABSTRACT

The invention relates to new prothrombin mutants or derivatives thereof which comprise one or more changes in their protein sequence as compared to natural protein, are either inactive or have an activity of approximately 10% at the most, preferably approximately 0.25% at the most, of the natural protein and which have a binding capacity relative to natural ligands (natural or synthetic anticoagulants) substantially corresponding to that of the natural protein. Furthermore, the use of mutated prothrombin mutants or derivatives, respectively, as pharmaceutical preparations is described.

22 Claims, 14 Drawing Sheets

FIG. I-A

```
           -43 (Preprothrombin)
Frame 1   Met Ala His Val Arg Gly Leu Gln Leu Pro Gly Cys Leu Ala Leu Ala Ala Leu Cys
          ATG GCG CAC GTC CGA GGC TTG CAG CTG CCT GGC TGC CTG GCC GTG GCT GCC GTG TGT
                       9          18          27          36          45          54

Ser Leu Val His Ser Gln His Val Phe Leu Ala Pro Gln Gln Ala Arg Ser Leu Leu Gln Arg
          AGC CTT GTG CAC AGC CAG CAT GTG TTC CTG GCT CCT CAG CAA GCA CGG TCG CTG CTC CAG CGG
                       66          75          84          93         102         111         120

+1 (Prothrombin)
          Val Arg Arg Ala Asn Thr Phe Leu Glu Glu Val Arg Lys Gly Asn Leu Glu Arg Glu Cys Val
          GTC CGG CGA GCC AAC ACC TTC TTG GAG GAG GTG CGC AAG GGC AAC CTA GAG CGA GAG TGC GTG
                      129         138         147         156         165         174         183

Glu Glu Thr Cys Ser Tyr Glu Glu Ala Phe Glu Ala Leu Glu Ser Ser Thr Ala Thr Asp Val
          GAG GAG ACG TGC AGC TAC GAG GAG GCC TTC GAG GCT CTG GAG TCC TCC ACG GCT ACG GAT GTG
                      192         201         210         219         228         237         246

Phe Trp Ala Lys Tyr Thr Ala Cys Glu Thr Ala Arg Thr Pro Arg Asp Lys Leu Ala Ala Cys
          TTC TGG GCC AAG TAC ACA GCT TGT GAG ACA GCG AGG ACG CCT CGA GAT AAG CTT GCT GCA TGT
                      255         264         273         282         291         300         309

Leu Glu Gly Asn Cys Ala Glu Gly Leu Gly Thr Asn Tyr Arg Gly His Val Asn Ile Thr Arg
          CTG GAA GGT AAC TGT GCT GAG GGT CTG GGT ACG AAC TAC CGA GGG CAT GTG AAC ATC ACC CGG
                      318         327         336         345         354         363         372

Ser Gly Ile Glu Cys Gln Pro Trp Arg Ser Arg Tyr Pro His Lys Pro Glu Ile Asn Ser Thr
          TCA GGC ATT GAG TGC CAG CCA TGG AGG AGT CGC TAC CCA CAT AAG CCT GAA ATC AAC TCC ACT
                      381         390         399         408         417         426         435

Thr His Pro Gly Ala Asp Leu Gln Glu Asn Phe Cys Arg Asn Pro Asp Ser Ser Thr Met Gly
          ACC CAT CCT GGG GCC GAC CTA CAG GAG AAT TTC TGC CGC AAC CCC GAC AGC AGC ACC ATG GGA
                      444         453         462         471         480         489         498

Pro Trp Cys Tyr Thr Thr Asp Pro Thr Val Arg Arg Gln Glu Cys Ser Ile Pro Val Cys Gly
          CCC TGG TGC TAC ACT ACA GAC CCC ACC GTG AGG AGG CAG GAA TGC AGC ATC CCT GTC TGT GGC
                      507         516         525         534         543         552         561

Gln Asp Gln Val Thr Val Ala Met Thr Pro Arg Ser Glu Gly Ser Ser Val Asn Leu Ser Pro
          CAG GAT CAA GTC ACT GTA GCG ATG ACT CCA CGC TCC GAA GGC TCC AGT GTG AAT CTG TCA CCT
                      570         579         588         597         606         615         624
```

FIG. I-B

```
Pro Leu Glu Gln Cys Val Pro Asp Arg Gly Gln Gln Tyr Gln Gly Arg Leu Ala Val Thr Thr
CCA TTG GAG CAG TGT GTC CCT GAT CGG GGG CAG CAG TAC CAG GGG CGC CTG GCG GTG ACC ACA
        633         642         651         660         669         678         687

His Gly Leu Pro Cys Leu Ala Trp Ala Ser Ala Gln Ala Lys Ala Leu Ser Lys His Gln Asp
CAT GGG CTC CCC TGC CTG GCC TGG GCC AGC GCA CAG GCC AAG GCC CTG AGC AAG CAC CAG GAC
        696         705         714         723         732         741         750

Phe Asn Ser Ala Val Gln Leu Val Glu Asn Phe Cys Arg Asn Pro Asp Gly Asp Glu Glu Gly
TTC AAC TCA GCT GTG CAG CTG GTG GAG AAC TTC TGC CGC AAC CCA GAC GGG GAT GAG GAG GGC
        759         768         777         786         795         804         813

Val Trp Cys Tyr Val Ala Gly Lys Pro Gly Asp Phe Gly Tyr Cys Asp Leu Asn Tyr Cys Glu
GTG TGG TGC TAT GTG GCC GGG AAG CCT GGC GAC TTT GGG TAC TGC GAC CTC AAC TAT TGT GAG
        822         831         840         849         858         867         876

Glu Ala Val Glu Glu Glu Thr Gly Asp Gly Leu Asp Glu Asp Ser Asp Arg Ala Ile Glu Gly
GAG GCC GTG GAG GAG GAG ACA GGA GAT GGG CTG GAT GAG GAC TCA GAC AGG GCC ATC GAA GGG
        885         894         903         912         921         930         939

Arg Thr Ala Thr Ser Glu Tyr Gln Thr Phe Phe Asn Pro Arg Thr Phe Gly Ser Gly Glu Ala
CGT ACC GCC ACA AGT GAG TAC CAG ACT TTC TTC AAT CCG AGG ACC TTT GGC TCG GGA GAG GCA
        948         957         966         975         984         993        1002

293 (Prothrombin)
Asp Cys Gly Leu Arg Pro Leu Phe Glu Lys Lys Ser Leu Glu Asp Lys Thr Glu Arg Glu Leu
GAC TGT GGG CTG CGA CCT CTG TTC GAG AAG AAG TCG CTG GAG GAC AAA ACC GAA AGA GAG CTC
       1011        1020        1029        1038        1047        1056        1065

Faktor Xa
                       ↓+1 [Thrombin]
Leu Glu Ser Tyr Ile Asp Gly Arg Ile Val Glu Gly Ser Asp Ala Glu Ile Gly Met Ser Pro
CTG GAA TCC TAC ATC GAC GGG CGC ATT GTG GAG GGC TCG GAT GCA GAG ATC GGC ATG TCA CCT
       1074        1083        1092        1101        1110        1119        1128

Trp Gln Val Met Leu Phe Arg Lys Ser Pro Gln Glu Leu Leu Cys Gly Ala Ser Leu Ile Ser
TGG CAG GTG ATG CTT TTC CGG AAG AGT CCC CAG GAG CTG CTG TGT GGG GCC AGC CTC ATC AGT
       1137        1146        1155        1164        1173        1182        1191

43 [Thrombin]
                  363 (Prothrombin)
Asp Arg Trp Val Leu Thr Ala Ala His Cys Leu Leu Tyr Pro Pro Trp Asp Lys Asn Phe Thr
GAC CGC TGG GTC CTC ACC GCC GCC CAC TGC CTC CTG TAC CCG CCC TGG GAC AAG AAC TTC ACC
       1200        1209        1218        1227        1236        1245        1254

Glu Asn Asp Leu Leu Val Arg Ile Gly Lys His Ser Arg Thr Arg Tyr Glu Arg Asn Ile Glu
GAG AAT GAC CTT CTG GTG CGC ATT GGC AAG CAC TCC CGC ACC AGG TAC GAG CGA AAC ATT GAA
       1263        1272        1281        1290        1299        1308        1317
```

FIG. I-C

Lys Ile Ser Met Leu Glu Lys Ile Tyr Ile His Pro Arg Tyr Asn Trp Arg Glu Asn Leu Asp
AAG ATA TCC ATG TTG GAA AAG ATC TAC ATC CAC CCC AGG TAC AAC TGG CGG GAG AAC CTG GAC
    1326         1335         1344         1353         1362         1371         1380

99 [Thrombin]
      419 (Prothrombin)
Arg Asp Ile Ala Leu Met Lys Leu Lys Lys Pro Val Ala Phe Ser Asp Tyr Ile His Pro Val
CGG GAC ATT GCC CTG ATG AAG CTG AAG AAG CCT GTT GCC TTC AGT GAC TAC ATT CAC CCT GTG
    1389         1398         1407         1416         1425         1434         1443

119 [Thrombin]
439 (Prothrombin)
Cys Leu Pro Asp Arg Glu Thr Ala Ala Ser Leu Leu Gln Ala Gly Tyr Lys Gly Arg Val Thr
TGT CTG CCC GAC AGG GAG ACG GCA GCC AGC TTG CTC CAG GCT GGA TAC AAG GGG CGG GTG ACA
    1452         1461         1470         1479         1488         1497         1506

Gly Trp Gly Asn Leu Lys Glu Thr Trp Thr Ala Asn Val Gly Lys Gly Gln Pro Ser Val Leu
GGC TGG GGC AAC CTG AAG GAG ACG TGG ACA GCC AAC GTT GGT AAG GGG CAG CCC AGT GTC CTG
    1515         1524         1533         1542         1551         1560         1569

Gln Val Val Asn Leu Pro Ile Val Glu Arg Pro Val Cys Lys Asp Ser Thr Arg Ile Arg Ile
CAG GTG GTG AAC CTG CCC ATT GTG GAG CGG CCG GTC TGC AAG GAC TCC ACC CGG ATC CGC ATC
    1578         1587         1596         1605         1614         1623         1632

Thr Asp Asn Met Phe Cys Ala Gly Tyr Lys Pro Asp Glu Gly Lys Arg Gly Asp Ala Cys Glu
ACT GAC AAC ATG TTC TGT GCT GGT TAC AAG CCT GAT GAA GGG AAA CGA GGG GAT GCC TGT GAA
    1641         1650         1659         1668         1677         1686         1695

205 [Thrombin]
      525 (Prothrombin)
Gly Asp Ser Gly Gly Pro Phe Val Met Lys Ser Pro Phe Asn Asn Arg Trp Tyr Gln Met Gly
GGT GAC AGT GGG GGA CCC TTT GTC ATG AAG AGC CCC TTT AAC AAC CGC TGG TAT CAA ATG GGC
    1704         1713         1722         1731         1740         1749         1758

Ile Val Ser Trp Gly Glu Gly Cys Asp Arg Asp Gly Lys Tyr Gly Phe Tyr Thr His Val Phe
ATC GTC TCA TGG GGT GAA GGC TGT GAC CGG GAT GGG AAA TAT GGC TTC TAC ACA CAT GTG TTC
    1767         1776         1785         1794         1803         1812         1821

Arg Leu Lys Lys Trp Ile Gln Lys Val Ile Asp Gln Phe Gly Glu Stop
CGC CTG AAG AAG TGG ATA CAG AAG GTC ATT GAT CAG TTT GGA GAG TAG
    1830         1839         1848         1857         1866

FIG. 2

```
Restriction sites (mut. Prothrombin-PCR-fragment)              (Ecl136II)
Amino acids(mut. Prothrombin-PCR-fragment)                              Ser   Met  Leu
5'-Primer #2041                       (5'-T AAC TGA CGG TCC TT(G AG/C TC)C  ATG  TTG Restriction sites (mut. Prothrombin)                    (EcoRV/Ecl136II)
Amino acids(mut. Prothrombin)        Arg  Asn  Ile  Glu  Lys    Ile  Ser   Met  Leu
Prothrombin mut. construct      (5'-G CGA  AAC  ATT  GAA  AA(G  AT/C TC)C  ATG  TTG DNA-sequence(wt Prothrombin)    (5'-G CGA  AAC  ATT  GAA  AA(G  AT/A TC)C  ATG  TTG
Amino acids(wt Prothrombin)          Arg  Asn  Ile  Glu  Lys    Ile  Ser   Met  Leu
Restriction sites (wt Prothrombin)                            (EcoRV)
```

```
                                                 (SspI)
Glu  Lys  Ile  Tyr  Ile......Arg  Glu  Asn  Leu  Asp  Arg   Asn   Ile  Ala  Leu  Met
GAA  AAG  ATC  TAC  ATC....G CGG  GAG  AAC  CTG  GAC  CGG  (AAT   ATT) GCC  CTG  ATG (SspI)
Glu  Lys  Ile  Tyr  Ile......Arg  Glu  Asn  Leu  Asp  Arg   Asn   Ile  Ala  Leu  Met
GAA  AAG  ATC  TAC  ATC....G CGG  GAG  AAC  CTG  GAC  CGG  (AAT   ATT) GCC  CTG  ATG

GAA  AAG  ATC  TAC  ATC....G CGG  GAG  AAC  CTG  GA(C  CGG  G)AC  ATT  GCC  CTG  ATG
Glu  Lys  Ile  Tyr  Ile......Arg  Glu  Asn  Leu  Asp   Arg  Asp   Ile  Ala  Leu  Met
                                                            (NciI)
```

```
                                                  (DraIII)
Lys  Leu  Lys  Lys  Pro  Val  Ala  Phe  Ser  Asp  Tyr  Ile   His  Pro  Val   Cys  Leu
AAG  CTG  AAG  AAG  CCT  GTT  GCC  TTC  AGT  GAC  TAC  ATT  (CAC  CCT/GTG)   TGT  CTG (DraIII)
Lys  Leu  Lys  Lys  Pro  Val  Ala  Phe  Ser  Asp  Tyr  Ile   His  Pro  Val   Cys  Leu
AAG  CTG  AAG  AAG  CCT  GTT  GCC  TTC  AGT  GAC  TAC  ATT  (CAC  CCT/GTG)   TGT  CTG

Lys  Leu  Lys  Lys  Pro  Val  Ala  Phe  Ser  Asp  Tyr  Ile   His  Pro  Val   Cys  Leu
AAG  CTG  AAG  AAG  CCT  GTT  GCC  TTC  AGT  GAC  TAC  ATT  (CAC  CCT/GTG)   TGT  CTG
                                                                  (DraIII)
```

C-3' Sequence complementary to primer #2066

C-3' Sequence complementary to primer #2066

C-3'

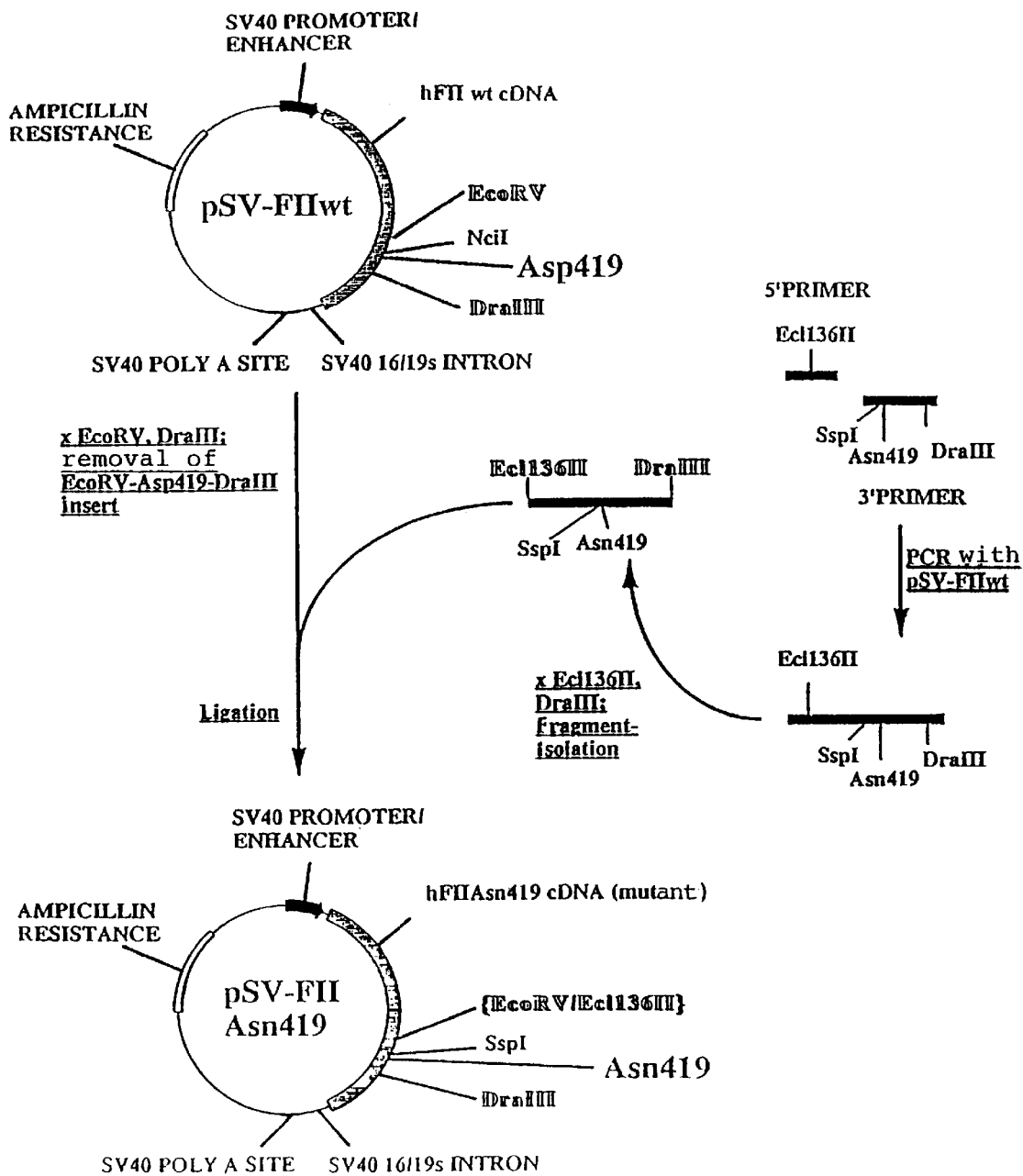
FIG. 3-A

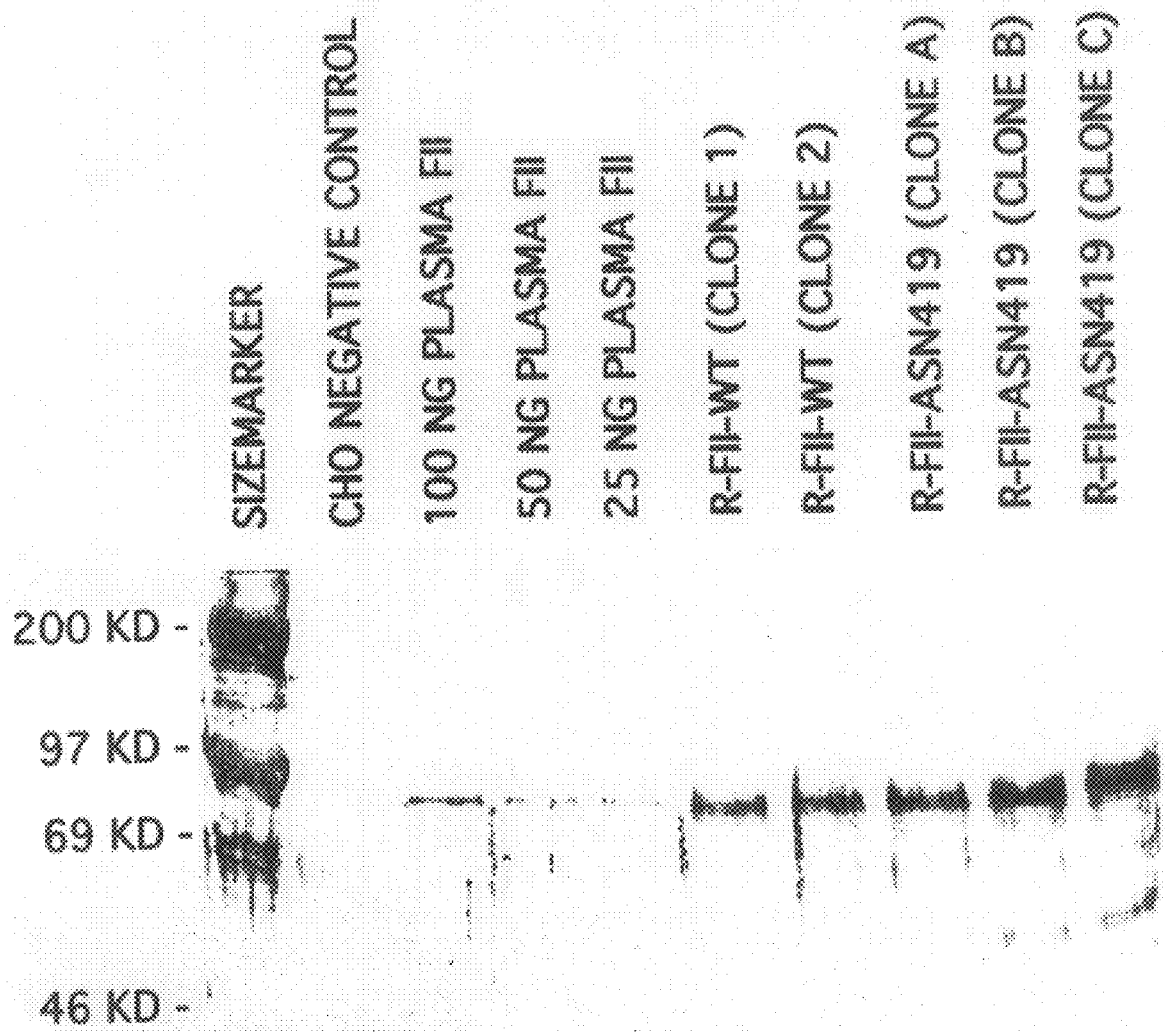
FIG. 3-B

PROTHROMBIN DERIVATIVES

The invention relates to new prothrombin mutants or derivatives thereof which may be utilized as antagonists of their natural functions.

BACKGROUND OF THE INVENTION

The mechanism of blood coagulation normally occurs in a cascade of two possible routes. One of the routes, the so-called extrinsic blood coagulation, starts with the liberation of thromboplastin and the activation of factor VII. Activated factor VII in turn activates factor X, followed by an activation of factor V and factor II (prothrombin). Factor IIa (thrombin) converts fibrinogen into fibrin at the end of the cascade.

The other route, the so-called intrinsic blood coagulation, occurs via an activation of factor XII by contact with and subsequent activation of factor XI, factor IX and factor X in the presence of calcium and factor VIII, followed by an activation of factor II to factor IIa which triggers the coagulation by cleaving fibrinogen to fibrin. Thus, factor IIa plays a central role in both routes of the blood coagulation cascade. Hitherto, there has been an intensive search for anticoagulants which may particularly be utilized in the treatment of septic shock, thromboses, embolisms, arteriosclerosis and cardiac infarctions, furthermore in case of blood transfusions or following surgery. One method of suppressing the coagulation of blood is the direct administration of substances which inhibit thrombin.

Hitherto, heparin or coumarin have been utilized as anticoagulants. They are, however, relatively systemic and increase the risk of inner hemorrhages. Hirudin, on the other hand, is extremely specific in its binding to thrombin and offers further advantages as compared to the other anticoagulants. It does not require endogenous cofactors, is pharmacodynamically inert, exhibits no effect on blood cells, plasma proteins (with the exception of thrombin) or enzymes, and is immunogenic on account of its small molecular size. Furthermore, hirudin is not stored in organs and is excreted unchanged in urine.

Hirudin is a single-chain polypeptide of 65 amino acids which is naturally formed by the medicinal leech (Hirudo medicinalis) in its secretory glands. Hirudin acts as extremely strongly binding and highly specific inhibitor for the protease thrombin and prevents blood coagulation. The mechanism of the effect of hirudin as thrombin inhibitor has been cleared up: The C-terminal part of hirudin binds to the anion binding sites of the thrombin and thus occupies the binding site of the fibrinogen chain on thrombin. In addition, the N-terminal part of hirudin blocks the active site of thrombin (Szyperski et al. 1992, J. Mol. Biol. 228: 1206–1211; Fenton et al. 1991, Blood Coagul. Fibrinol.2: 69–75; Rydel et al. 1990, Science 249: 277–280; Karshikov et al. 1992, Prot. Science 1: 727–735; Markwardt 1991, Thromb. Haemost. 66: 141–152). For this reason, there has already been an interest for quite some time in using hirudin as a specific anticoagulant.

Recently it has been possible to prepare large amounts of hirudin by a recombinant route, and to use them for pharmacological investigations (Rigel et al. 1993, Circl. Res. 72: 1091–1102; Loison et al. 1988, Biotechnol. 6: 72–77; Zawilska et al. 1993, Thromb. Res. 69: 315–320; Klöcking et al. 1990, Blut 60: 129; Fareed and Walenga 1989, FASEB J. 3: 328; Markwardt et al. 1988, Pharmazie 43: 202–207). There result several clinical applications for hirudin: in hemodialysis, as an anticoagulant during the pulmonary transluminal coronary angioplasty (PTCA), for the prophylaxis of post-operative thrombosis, for the prevention of rethrombosis, for microvascular surgery, as anti-coagulant in hemodialysis and in case of extracorporeal circulation, as an admixture to thrombolytic agents, such as, e.g., plasminogen activators and streptokinase, as anticoagulant during surgery and for the clinical suppression of coagulation.

When administering anticoagulants, exact dosing, however, is difficult. For instance, the inhibition of thrombin in the circulation of blood caused by hirudin can lead to undesired complications and hemorrhages requiring an immediate elimination of hirudin from circulation (Fareed et al. 1991, Sem. Thromb. Hemost. 17: 137–144; Brüggener et al. 1989, Pharmazie 44: 648–649; Fareed and Walenga 1989, FASEB J. 3: 328). Yet the determination of the hirudin level (differentiation of free and bound hirudin) in the blood and monitoring the course of the hirudin excretion are possible only indirectly via the determination of the thrombin activity. At present, it is only possible to reduce the hirudin level in blood by natural excretion and, optionally, by means of dialysis. The administration of prothrombin has also been suggested (Walenga et al. Sem. Thromb. Hemost. 15:316:1989), yet the conversion of prothrombin into thrombin is time-dependent in circulation. On the other hand, an excess of thrombin favours the coagulation tendency. Not least of all, hirudin does form a very strong complex with thrombin which is difficult to dissociate even in vitro so that dosing of the hirudin level via a displacement mechanism realistically has not been practicable so far.

Thus there has been an intensive search in the prior art for a suitable antagonist to hirudin which can be used purposefully and thus does not exhibit side effects as regards blood coagulation. Although this has been a known problem of hirudin research (Markwardt F., Haemostasis 21:11; 1991), to date there have not been any practicable solutions which could be used in medicine.

It has been suggested (Brüggener et al., Pharmazie 44:648; 1989) to carry out a chemical change of the thrombin. For this, diisopropyl fluorophosphate that has been purified from plasma was coupled to thrombin. DIP accumulates at the active site of thrombin, thereby changing the three-dimensional structure of the catalytic region. The DIP-thrombin formed is enzymatically inactive, yet binds hirudin. However, diisopropyl fluorophosphate is extremely toxic and dangerous. Since the binding of DIP to thrombin is not very stable, DIP can easily dissociate therefrom. A DIP-thrombin complex disintegrating in vivo thus is completely unsuitable for a clinical application.

In WO 93/15757 prothrombin intermediates have been suggested as antidotes to hirudin. However, these products comprise the usual risks generally inherent in preparations obtained from plasma, e.g. contamination by human pathogenic viruses.

Beside the use of heparin, coumarin and hirudin for preventing blood coagulation, also synthetic thrombin inhibitors, such as NAPAP (Na-(2-naphthyl-sulfurylglycyl)-D,L-amidinophenyl-alanin peptide) or PPACK (D-Phe-Pro-Arg-CHCl) are known. Furthermore, it has i.a. been contemplated to use modified proteins, such as, e.g., inactivated coagulation factors, directly as anticoagulants. There, one particular problem is that in vivo the modified protein possibly could be eliminated from blood more rapidly than the wild type protein. The coagulation process, comprising the cooperation of the intrinsic and extrinsic blood coagulation cascade and cell surface receptors, is very complex. Thus, apart from its greatly reduced or completely inhibited coagulation activity, an inactivated coagulation factor usable in vivo for therapy or prophylaxis should not differ from the natural protein in any further essential property, such as, e.g., receptor binding capacity. An in vivo half-life of the inactive protein corresponding to that of the active coagulation factor or even longer than that would be desirable. Since particularly thrombin has a very short half-life in vivo, an inactive coagulation factor having an extended half-life would increasingly displace the active protein, e.g. thrombin, from its receptor in case of a competitive inhibition. This would have the advantage that merely a relatively low dose would have to be administered for an efficient anticoagulant action of the inactive protein.

SUMMARY OF THE INVENTION

The present invention thus has as its object to provide a medically usable antagonist of hirudin which is substantially free from an enzymatic activity that promotes blood coagulation.

A further object of the present invention consists in providing an inactive coagulation factor which, in terms of its essential properties, such as, e.g., receptor binding capacity, does not differ from the natural protein and whose in vivo half-life optionally is increased.

According to the invention, this object is achieved by new prothrombin mutants or derivatives thereof which have one or more changes in their protein sequence as compared to the natural protein, are either inactive or have an activity of approximately 10% at the most, preferably approximately 0.25% at the most, of the natural protein and in which the change of the protein sequence does not affect their binding capacity to thrombin-specific ligands and receptors, such as natural and synthetic anticoagulants. Functionally, the inventive prothrombin mutants or their derivatives do not differ from their naturally occurring protein except for a greatly or completely reduced coagulation activity and optionally a changed in vivo half-life.

Within the scope of the present invention, by mutated prothrombin mutants or derivatives thereof, all the proteins derivable from the protein sequence of prothrombin are to be understood which exhibit the essential binding determinants of thrombin that are necessary for binding to the thrombin-specific natural and synthetic anticoagulants. Thus, the structure of the prothrombin mutant possibly should not be changed too much by the mutations as compared to wild type protein or its proteolytic derivatives, respectively, so that an optimum binding to the ligands, in particular to the natural ligands, is ensured.

Thus, an essential prerequisite for the mutants and derivatives according to the invention is that the change of the protein sequence does not affect their binding capacity to thrombin-specific ligands and receptors, such as natural and synthetic anticoagulants.

It has to be assumed that the mutants or derivatives, respectively, according to the invention must have a binding capacity of at least 80% of the binding capacity of natural thrombin, so that the binding capacity can be considered as not affected. Also mutants and derivatives, respectively, which have a higher binding capacity than natural thrombin are, of course, also within the scope of the present invention.

The amount of binding capacity can be analyzed by any suitable method, e.g. by anticoagulants-competitive analysis between mutant or derivative, respectively, and natural thrombin (Gan et al., 1993), by assays relating to the binding affinity relative to artificial inhibitors (e.g. with DAPA (=dansyl arginine-N-(3-ethyl-1,5-pentandiyl)amide); Pei et al., J. Biol. Chem. 266: 9598, 1991), or by means of tests of the binding affinity on an immobilized natural and synthetic anticoagulant or inhibitor, respectively.

In case of the latter, the natural or synthetic anticoagulant or the inhibitor, respectively, is immobilized on a solid matrix, a sample containing a certain amount of the derivative to be assayed is contacted with the natural and the synthetic anticoagulant or the inhibitor, respectively, the amount of bound mutant or derivative, respectively, is determined, and the results are correlated by means of a parallel determination with natural thrombin.

The mutants or derivatives, respectively, according to the invention preferably should be entirely inactive, i.e. they should not have any thrombin or thrombin-analogous activity. However, derivatives having a slight activity can also be used successfully according to the invention, since an activity of approximately 10% at the most, in particular 0.25% at the most, of natural thrombin generally does not lead to the undesired side effects, such as, e.g., coagulation tendency, when the derivatives according to the invention are administered.

The mutants or derivatives, respectively, according to the invention are further characterized in that they can form a complex with hirudin and thus are able to neutralize hirudin. Furthermore, they can dissociate a complex consisting of plasmatic or recombinant wt-thrombin with hirudin, and complex the thus liberated hirudin. From this follows furthermore that the liberated plasmatic or recombinant wild type (wt) thrombin is active again and can fulfill its task in blood coagulation. Also according to the invention this is a necessary parameter for the therapeutic use of the thrombin derivatives.

Preferred embodiments of the mutants or derivatives, respectively, according to the invention have an in vivo half-life of more than one hour.

Other preferred embodiments have an in vivo half-life of 10 minutes at the most.

The change of the amino acid sequence may consist of an exchange of one or more amino acids, it may, however, also consist of a deletion, preferably a deletion corresponding to the processing procedure during the activation of prothrombin, or of an insertion, if by these changes the parameter essential to the invention, an activity of approximately 10% at the most, in particular of 0.25% at the most, of natural thrombin, and an almost unchanged binding to thrombin ligands and -receptors, are met. The term "derivative" is meant to include both the proteins changed merely by mutation and the processed mutant proteins. For the exchange of amino acids, those are best suited as amino acids to be introduced which have as little influence as possible on the spacial structure of the protein. These are either very small amino acids, such as alanin, or amino acids which are very similar to the original amino acid and differ therefrom only by one functional group, e.g. asparagine and aspartic acid.

The parameters according to the invention make the mutants or derivatives, respectively, mentioned to ideal thrombin inhibitor antagonists, since they do not have the disadvantages mentioned in the prior art, i.e. an undesired coagulation activity, toxicity or a lack of efficiency or specificity, respectively.

Since the inventive mutants or derivatives, respectively, are inactive or have an activity of approximately 10% at the most, in particular approximately 0.25% at the most, of natural thrombin (whereby the in vivo thrombin activity of the mutants or derivatives, respectively, is even considerably lower than these approximately 0.25%), they cannot lead to undesired coagulation effects even if they are administered in an overdose.

For the mutants or derivatives, respectively, according to the invention, a toxic effect is not to be expected, since they hardly differ from the natural proteins and thus can be metabolized normally.

The mutants or derivatives, respectively, according to the invention are highly efficient and highly specific as antagonists, since their binding determinants to natural and synthetic inhibitors are substantially unchanged and correspond to those of natural thrombin.

Preferred changes of the protein sequence concern amino acids from the active site of the prothrombin, meizothrombin or thrombin molecule, in particular the amino acids His-363 and Asp-419, based on the amino acid numbering in human prothrombin according to FIG. 1. (The numbering of the amino acids in general is according to FIG. 1, in which the cDNA sequence and the amino acid sequence of prothrombin are shown. The cleavage sites of factor Xa are indicated in the cDNA sequence so that the cDNA and amino acid sequence of thrombin can be derived. Numbering starts with the 1st amino acid of the mature prothrombin after cleavage of the leader sequence and the propeptide. The cDNA sequence of prothrombin is illustrated in SEQ.ID.NO.8, the amino acid sequence in SEQ.ID.NO.9.).

Particularly the amino acid Aspartic acid-419 (Asp-419) has no close contact to bound hirudin, and therefore the exchange of this amino acid is particularly preferred within the scope of the present invention.

In addition, the changes relating to the cysteine residues Cys-293 and Cys-439, based on the amino acid numbering in prothrombin according to FIG. 1, are also preferred. These mutations enable the formation of a single-chain thrombin derivative (since the sulphur bridge bond between the B-chain and the A-chain is prevented), which finally does not have any enzymatic activity despite its binding capacity to hirudin (since the A-chain is missing). In this case, the amino acids serine and alanine offer themselves as exchange partners.

Since all these selected derivatives have mutations which directly concern the catalytic center or concern disulfide bonds important for the function of thrombin, respectively, they are inactive. As can be seen by way of structural data (Rydel et al., 1990), these amino acids neither concern regions that concern the binding of natural and synthetic inhibitors, in particular hirudin.

Thus, the invention preferably relates to prothrombin mutants or -derivatives in which at least one amino acid selected from His-363 or Asp-419 and optionally Cys-293 or Cys-439, has been changed, in particular Asp-419-mutants.

A particularly preferred embodiment of the mutants or derivatives, respectively, according to the invention relates to mutants or derivatives, respectively, in which the amino acid Asp-419 has been exchanged for Asn.

It has been shown that this variant is inactive, even towards the synthetic substrate AcOH-H-D-CHG-Ala-Arg-pNA it has merely a residual activity of approximately 0.25%, so that no coagulation-active side effects whatsoever are to be expected. Furthermore, the binding capacity of this derivative, e.g. relative to hirudin, cannot be differentiated from that of natural thrombin, since the structural changes brought about by the exchange of Asp for Asn is very slight and moreover is localized in a region of the protein which does not concern the binding to the natural and synthetic inhibitors, in particular hirudin.

Mutant prothrombines have been described in the prior art, yet derivatives exhibiting the properties claimed have not yet been disclosed. Yet it is just these properties that make the use of the prothrombin, meizothrombin and thrombin derivatives according to the invention so very advantageous.

A series of genetic defects have, e.g., been described which relate to prothrombins and thrombins resulting therefrom with point mutations, the various mutants having a drastically reduced blood coagulation activity (Henriksen R. A., Methods in Enzymology, Vol. 222:312 (1993)). Yet all these mutations concern changes in which a certain—though reduced—thrombin activity is still found (particularly relative to synthetic substrates). Yet it is probably this residual activity which allows for the survival of persons suffering from these defects, and from this it follows that a mutation that leads to an entirely inactive thrombin probably is not capable of surviving.

Furthermore, in vitro point mutations have been carried out in the prothrombin- and thrombin sequence so as to carry out structural and functional analyses:

For instance, Serine-528 at the active site of bovine prothrombin (equivalent to Serine-525 in the corresponding human prothrombin) has been mutated to an alanine. With such a mutant prothrombin, experiments relating to the fundamentals of science have been carried out to study the influence of this mutation on the expression, γ-carboxylation and activation of prothrombin.

The structural analysis of the thrombin-hirudin complex has shown that also amino acids from the active site of thrombin contribute slightly to the formation of the complex. Thus, in particular Ser-525 in human prothrombin may form hydrogen bridges to the N-terminal amino acid of hirudin and may be within the radius of 3.2 Å from the N-terminus of hirudin. Thus, Ser-525 apparently contributes to the bonding of hirudin (Rydel at al., Science 249:277, 1990).

Furthermore, it has been found that the bovine Ser-528 variant merely has a 74% binding capacity relative to DAPA, as compared to natural thrombin. This was proof of the assumption that this serine residue is located immediately in the DAPA or hirudin binding determinant, respectively. Therefore, mutations which merely concern the Ser-528 site in bovine prothrombin or the Ser-525 site in human prothrombin, respectively, do not meet the requirement of the sufficient binding capacity to the inhibitor.

Furthermore, thrombin fragments with longer deletions have been prepared (Gan et al., Arch. Biochem. Biophys. 1993:301, 228). A degradation product of thrombin, ζ-thrombin, is obtained which comprises the amino acids 469 to 579 of the α-thrombin sequence. For functional studies, the amino acids Arginine-517 (to glutamine), and Serine-525 (to alanine), respectively, were mutated, and there a slighter activity was found in the individual mutants than in wild type thrombin. The hirudin binding capacity was only partly maintained in some ζ-thrombins. The Ser-525-Ala mutant did exhibit the least enzymatic activity and the best results in terms of hirudin binding, yet also in these studies the binding capacity was clearly below that of natural thrombin. It has been shown that in competitive binding studies the thrombin fragments compete to different degrees with a thrombin-hirudin binding, and there are no absolute data regarding the binding capacity of the fragments to hirudin, yet the results clearly show that the binding capacity to hirudin has been markedly reduced by the mutation.

Thus, these ζ-thrombins are not suitable for the object underlying the invention: as compared to wild type thrombins, they are greatly changed, and an optimum bonding to the natural ligands cannot be guaranteed.

Thus, it has not been possible to meet the required parameters with the prothrombin- or thrombin derivatives, respectively, described in the prior art.

Neither can any data be found in these citations as to a possible therapeutic or diagnostic utilization of these prothrombin mutants (derivatives) or ζ-thrombin fragments.

Thus, according to another aspect, the present invention relates to the use of prothrombin mutants or derivatives thereof as medicaments, in particular for producing a medical preparation for preventing the side effects in an anticoagulation treatment, or as diagnostic agents. This use according to the invention of the mutants or derivatives, respectively, is particularly preferred in the anticoagulation treatment with hirudin, heparin, antithrombin III and/or the derivatives thereof, as well as synthetic inhibitors.

The medical treatment according to the invention thus comprises administering an effective dose of the prothrombin mutant or derivatives thereof to a patient, preferably intravenously. The effective dose will depend on each individual single case and preferably should be optimized by using the results obtained from a thrombin and/or hirudin determination.

Naturally, with the use according to the invention, the prothrombin mutants or derivatives, respectively, having the properties according to the invention as regards a deficient thrombin activity and a sufficient binding capacity are preferably used, yet under certain conditions also known derivatives can be utilized, in particular those which are largely inactive, such as, e.g., an analogue to the above-described bovine Ser-528 mutant (or its thrombin derivative, respectively), in which case, however, the drawback of the inferior binding capacity must be put up with.

It has generally been known that the in vivo half-life of the proteins in blood circulation is influenced by glycosylation. Proteins from mammalian cells thus may be present in glycosylated form via protein-surface-localized amino acid side-chains of asparagine (N-glycosylation) and serine/threonine (O-glycosylation). By the glycosylation of circulating proteins, a delay of their elimination from circulation, i.e. an extension of their half-life, is attained. Recombinant proteins prepared by manipulating mammalian cells by their nature are provided with the glycosylations common and natural for mammals and thus correspond to the surface structure of the corresponding human proteins.

By mutation of amino acids located at the surface of a protein, such as, e.g. asparagine (Asn) and serine (Ser), respectively, or threonine (Thr), into a different amino acid, or by deletion of one of these amino acids, it is, e.g., possible to prevent native glycosylation. It is known that slightly or non-glycosylated proteins are much more rapidly eliminated from circulation, i.e. that their half-life is shortened.

To the contrary, by mutation and amino acid exchange of individual amino acids located at the protein surface, the number of glycosylation sites of a protein molecule may be increased, e.g. in asparagine, and thus also the in vivo half-like can be increased. Depending on the number of mutant, deleted or additionally inserted asparagine residues in the protein, the half-life thus optionally can be varied.

For the use according to the invention of the prothrombin mutants or derivatives thereof as antagonists relative to thrombin inhibitors, those mutants are particularly suitable, in which the half-life of the protein has been shortened by mutation. Preferably, thus, those mutants are used as antagonists which have a half-life of 10 minutes at the most.

The medical use according to the invention of the mutated prothrombin mutants or derivatives, respectively, also comprises their use as anticoagulants by competitive inhibition of thrombin, or as antagonists of their natural functions, respectively. This enables medical control of the blood coagulation by means of a product which is nearly identical to nature.

On account of the parameters according to the invention and of the unchanged binding capacity to specific receptors and ligands, prothrombin mutants or their derivatives are particularly useful as anticoagulants in vivo.

For the use according to the invention of the prothrombin mutants or derivatives thereof as anticoagulants, such mutants are particularly useful in which the half-life of the protein is increased by a purposeful amino acid exchange. Thus, preferably those inactive mutants are used as anticoagulants which have a half-life of more than 1 hour.

When using the prothrombin mutants of the invention as anticoagulants, they are processed after their application, corresponding to natural protein, in vivo to inactive thrombin which then is able to displace active thrombin occurring in blood from its receptors. The prothrombin mutant may optionally also be activated in vitro to the corresponding thrombin or meizothrombin mutant, and the activated form may directly be used for administration to the patient. Depending on the dosage of the prothrombin mutant or their derivatives according to the invention in a medicament, the blood coagulation can be slowed or completely stopped in vivo. The use of prothrombin mutants or derivatives thereof which are characterized by an increased in vivo half-life have the particular advantage that they circulate in blood substantially longer than their natural protein counterparts and thus can effectively influence blood coagulation. Moreover, for an effective anticoagulant action, the amount of therapeutically used protein may optionally also be correspondingly reduced.

For the in vivo application of the inventive prothrombin mutants or their derivatives as anticoagulants, a toxic side effect is not to be expected, since they are normally metabolized in vivo in accordance with their natural proteins.

The mutant prothrombin derivatives according to the invention may preferably be prepared by using recombinant DNA technology. Thus, the invention also relates to a method of preparing the inventive prothrombin mutants or their derivatives, respectively, in which the genetic information of prothrombin is mutated, preferably point-mutated, and expressed in a eukaryotic expression system, whereupon the expressed derivative is recovered.

There, preferably, human sequences are used.

In contrast to bacterial systems, the expression in eukaryotic systems has the advantage that also post-translational modifications, such as glycosylation and carboxylation, are carried out, and thus the expressed protein is better suited for an application on man.

For the recovery of the peptides in Gan et al., the mutated sequence portions of thrombin are expressed in *E. coli*, and the recombinant peptides are artificially provided with sulphur bridges in vitro. Accordingly, the yield of expressed thrombin-like structures suitable for tests was very low. The loss of the thrombin activity may be due to the absence of large parts of the thrombin sequence just as well as to the introduced mutations.

The expression in *E. coli*, as described in Gan et al., is not suitable for proteins having the properties according to the invention, since this expression system does not effect glycosylation, and also the folding of the expressed proteins does not correspond to the physiological structure. According to the invention, however, as few changes as possible should be made in the derivatives, as compared to wild type thrombin. For the functional studies in Gan et al. it is, however, without importance that the expressed ζ-thrombins do not comprise carbohydrates, on the one hand (the only glycosylation site in physiologic thrombin (Asparagine-53) was missing), and that the folding of the peptide in vitro has been carried out in a complicated way. This method leads only to extremely low yields.

In a method according to the present invention, the cDNA-sequence of human prothrombin or the cDNA-sequence of human thrombin preferably is point-mutated, whereby an exchange of at least one amino acid in the amino acid sequence is brought about. In the case of prothrombin, the site of mutation according to the invention is to be found in the region of the prothrombin sequence which, after activation of the prothrombin, lies in the thrombin sequence.

Preferably, the mutant prothrombin derivatives are expressed under the control of the SV40 promoter in CHO-DUXS B11 cells (Urlaub & Chasin, Proc. Natl. Acad. Sci. U.S.A. 77:4216, 1980). Yet, the expression may be effected with any common expression system, such as yeast, permanent cell lines or viral expression systems, and with any desired cell line which ensures that the protein is correctly processed and secreted in its functional form. Correct processing of the derivatives does not only encompass the complete glycosylation, but also the complete γ-carboxylation. Among the common eukaryotic expression systems are yeast, permanent cell lines (which have either been established by stable integration of the foreign-DNA in the chromosomes of the host cells, e.g. Vero, MRC5, CHO, BHK, 293, Sk-Hep1, in particular liver and kidney cells, or by using a vector which is permanently inherited in episomal state, e.g. vectors which are derived from papilloma viruses and grow, e.g., in C-127 cells), or viral expression systems, such as vaccinia virus, baculovirus or retroviral systems. As the cell lines, generally Vero, MRC5, CHO, BHK, 293, Sk-Hep-1, in particular liver and kidney cells, may be used.

Following the recovery of the expressed derivatives, still further processing steps may be carried out. One possibility of further processing prothrombin mutants or derivatives thereof, respectively, is a process step in which the prothrombin derivative is cleaved into meizothrombin analogues by means of a snake venom protease (e.g. Venom Protease). These meizothrombin analogues then also can be used as antagonists to the natural functions of thrombin, yet they do not exhibit an enzymatic thrombin activity. In this connection, all the methods known from the literature can be used.

Furthermore, a prothrombin derivative obtained may be cleaved into the thrombin derivative by means of trypsin, preferably immobilized trypsin. Yet, naturally any other common method of cleaving prothrombin to thrombin may be used, even those which use other suitable proteases, e.g. the snake venom from *E. carinatue* (Ecarin) or from *O. scvutellatus*.

To process the preparations, the derivatives according to the invention are either prepared with physiologic saline solution and optionally lyophilized, or they are lyophilized in distilled water and reconstituted with physiological saline solution before being administered. Alternatively, the preparations may also be kept available for use in other common solutions and/or with a pharmaceutical carrier or auxiliary agent.

According to the invention, the preparations are present in a form suitable for parenteral administration, i.e. for subcutaneous, intramuscular or intravenous administration.

A further advantage of the preparations according to the invention which must not be neglected consists in that on account of their production they are free from contaminations by viruses. Before being released for medical applications, the preparations may additionally be assayed for a possible contamination by residual nucleic acids of the expression cell line by means of a highly sensitive PCR method (e.g. disclosed in Austrian Patent Application A 1830/94), and if necessary, they may be purified once more.

Finally, the derivatives according to the invention must be tested for their capability of binding their natural ligands. Within the scope of the present invention, a test system has been worked out for this, in which the binding capacity of the (Pro-)thrombin derivatives to hirudin or hirudin derivatives is qualitatively and quantitatively analysed in a simple and reproducible manner. This test system consists in a solid matrix to which natural or recombinant hirudin, derivatives or peptides thereof are bound. Finally, the derivative according to the invention is bound to this immobilized hirudin and may be detected in a subsequent detection reaction.

Therefore, the invention also relates to a solid matrix to which natural or recombinant hirudin, derivatives or peptides thereof are bound, and their use in the determination of thrombin or thrombin derivatives. The determination may comprise both the quantitation and the determination of the binding capacity of the thrombin or thrombin derivative.

As solid matrix according to the invention any solid phase is to be understood, at which the natural and synthetic inhibitor can effectively be immobilized, e.g. natural polymers, such as cellulose, starch, dextrane, alginates, agarose, collagen, in particular the sepharose and cellulose materials, repsectively, widely used in immobilization technology, synthetic polymers, such as polyacryl amide, polyvinyl alcohol, methylacrylate, nylon or oxiranes which can easily be shaped to user-friendly devices, such as, e.g., microtiter plates, and finally inorganic materials, such as porous glasses, siliga gel, etc. (cf. also Römpp-Lexikon der Biotechnologie, pp. 385).

With the device according to the invention, a simple and precise determination of the thrombin or thrombin derivative concentration, respectively, can be effected, wherein not only the active thrombin itself can be determined, but also enzymatically inactive or only slightly active prothrombin or thrombin and derivatives therof. Furthermore, on account of its user-friendly design, the device according to the invention may also be indirectly used for the determination of the concentration of any thrombin-binding substances, such as thrombin inhibitors, yet particularly hirudin. Moreover, also a determination of the binding strength of thrombin or thrombin derivatives to the respective tested natural and synthetic inhibitors is feasible with the device according to the invention.

As thrombin or thrombin derivatives, all the proteins derivable from the protein sequence of prothrombin are to be understood within the scope of the present invention, in particular the mutant thrombin, meizothrombin or prothrombin derivatives described above. In this connection, the derivative can also be altered at the binding determinants, as long as this change does not exclude a bonding to the natural and synthetic inhibitors. The thrombin derivatives may differ from natural thrombin by one or more point deletion- or insertion mutations. Prothrombin derivatives, meizothrombin as well as the derivatives thereof may also be determined by means of the device according to the invention and are also to be viewed as thrombin derivatives within the scope of the present invention—insofar as their determination is concerned.

For the quantitation proper of thrombin, thrombin derivatives and/or hirudin or hirudin derivatives, according to the invention a test kit is provided which contains the device according to the invention as well as one or more containers with reagents for a specific detection reaction, preferably a thrombin-derivative-specific detection reaction. By specific detection reaction, any suitable detection reaction is to be understood, in particular those reactions which work with dyes (peroxidase, alkaline phosphatase, luminiscence reactions, biotin, avidin or biotin-streptavidin (as enhancer systems)) or radioactive determination methods.

For a determination of the concentration, preferably, the colour reaction which is simpler to handle is preferred to the radioactive determination. In particular, the peroxidase-labelled sheep-anti-thrombin-antibodies are used for the invention, and the substrate solutions common for the peroxidase reaction are used for the colour reaction.

The test kit according to the invention further includes a container with a physiologic buffer solution containing a carrier protein, whereby the reproducibility of the quantitation is substantially improved.

The specific detection reaction within the scope of the test kit of the invention preferably is a labelled thrombin-binding substance, since in the clinic, the determination of thrombin frequently is of primary importance as compared to the other determinable components. In the prior art a large number of labelled thrombin-binding substances is known. According to the invention, a dye-labelled polyclonal or monoclonal antibody to thrombin preferably is used. Detection by means of chromogenic substances is frequently preferred to radioactive determination methods, since the dye reactions do not entrain a radioactive contamination and since the rigid safety measures required when working with radioactive material very often render the radioactive determination method very impractical.

The detection method may take place according to the method steps common in protein chemistry. To determine the concentration of thrombin or thrombin derivatives, a thrombin solution is incubated for 15 minutes to 16 hours, preferably between 45 minutes and 4 hours, with the hirudin-coupled solid matrix. Usually, the reaction takes place in a physiologic buffer, preferably in a Tris-HCl buffer. It is particularly advantageous if a carrier protein, such as albumin, e.g., is admisted to the physiologic salt buffer.

A preferred embodiment of the test kit according to the invention further comprises a thrombin-containing reference solution which allows for the establishment of a reliable calibration straight line in the test system.

According to a further aspect, the invention relates to a method of quantitating thrombin or thrombin derivatives, which is characterized by the following steps:

incubating a solution which contains the amount of thrombin or thrombin derivatives to be quantitated with hirudin or a hirudin derivative which is immobilized on a solid matrix, the thrombin or derivative becoming bound to the immobilized hirudin or hirudin derivative, optionally removing non-bound thrombin or thrombin derivative, carrying out a specific detection reaction, the amount of bound thrombin or thrombin derivative being determined.

Carrying out the specific detection reaction may be effected either within the scope of the test kit according to the invention with the reagents for a specific detection reaction, or directly by a measuring device on the solid matrix itself, such as a sensor chip with a measuring installation connected therewith.

The method according to the invention may be carried out in a simple manner, it being particularly suited for the rapid and uncomplicated application in the clinical field.

A preferred embodiment of the method according to the invention relates to a method in which the specific detection reaction is a colour reaction, the concentration of thrombin or thrombin derivative being determined by correlation with the intensity of the colour reaction.

According to a further aspect, the method according to the invention also is suitable for quantitating hirudin or hirudin derivatives, such a method being characterized by the following steps:

incubating a solution comprising an amount of hirudin or hirudin derivative to be quantitated with a solution comprising a known amount of free thrombin or thrombin derivative, determining the free thrombin or thrombin derivative concentration remaining after incubation with the hirudin or hirudin derivative by means of the above-described method of the invention, and determining the amount of hirudin or hirudin derivative by calculating back on the basis of the differences between the amount of thrombin or thrombin derivative originally known and the amount determined.

According to a further aspect, the present invention relates to the use of a device according to the invention or of the test kit of the invention, respectively, for quantitating thrombin, thrombin derivatives and/or hirudin or hirudin derivatives as well as for determining the binding strength of thrombin or thrombin derivatives to hirudin or hirudin derivatives.

For, surprisingly, it has been shown that with this test kit it is possible for the first time also to determine the binding strength of thrombin or thrombin derivatives to hirudin or other thrombin-hampering substances. The binding strength of thrombin to hirudin primarily is of interest in case of thrombin derivatives whose binding properties to hirudin are unknown.

Furthermore, the test kit may be used for a function analysis of hirudin antagonists. When testing hirudin peptides or hirudin derivatives as effective anticoagulants, this method can also be applied.

The test kit according to the invention thus is suitable to answer all the questions arising in connection with thrombin, hirudin and the coagulation of blood in terms of concentration, binding strength and functionality. There, it must be particularly emphasized that due to the specificity of the binding of hirudin to thrombin, it is possible to obtain an extremely exact result. Impurities by other blood factors or proteins cannot falsify the result. Neither does the presence of prothrombin interfere with the analyses, since prothrombin does not bind to hirudin.

Although it has been known to couple hirudin to microtiter plates so as to test anti-hirudin-antibodies with these ELISA plates, a quantitation or determination of the binding capacity by aid of these plates has not yet been described. (Mille B. et al., Clin.Chem. 40:734, 1994).

When preparing a hirudin-coupled solid matrix, hirudin is coupled to the matrix in a buffer system.

Any buffer that is free from amino groups is suitable as buffer system, such as phosphate buffer, citrated buffer or preferably carbonate buffer. The pH of the buffer system should be in an amount of between 6 and 10, preferably at pH 9.3 to 9.7.

According to the invention, in the coupling reaction of hirudin to the solid carrier, it is incubated between one and 48 hours, preferably between one and 16 hours. The incubation time substantially depends on the incubation temperature, and in a coupling reaction, the incubation preferably takes place for 16 hours in the cold (4° C.), for two to three hours at room temperature, and for one hour at 37° C.

After the coupling reaction, according to the invention the excess non-bound hirudin is removed by means of a washing buffer comprised of a physiologic saline solution, preferably a Tris-HCl buffer. To this washing buffer a detergent, preferably Tween 20, may be added, the detergent concentration lying between 0.01 and 1%, preferably at 0.1%.

With the test kit according to the invention, concentrations of thrombin or thrombin derivatives in the range of from 0.1 pg/ml to 100 mg/ml, preferably in the range of from 0.1 ng/ml to 200 ng/ml thrombin, can be determined.

Not least of all, the inventive test kit is suitable for differentiating between thrombins with recombinant designed, purposeful mutations, deletions or insertions, it being possible to test whether or not the binding ability to hirudin has been maintained irrespective of the enzymatic activity.

This test according to the invention of the inventive test kit may especially be used if the thrombin level in blood is to be determined in case of a particular medical problem, so as to prevent thromboses by an exactly dosed administration of hirudin.

Furthermore, this test has the particular advantage that also thrombin can be determined which is not funcionally active and which thus is not detectable in tests that register the enzymatic activity of thrombin. This is, e.g., so in case of genetic defects, where there are physiologically inactive forms of thrombin.

The invention will now be explained in more detail and with reference to the following Examples and associated drawing figures to which, however, it shall not be restricted.

BRIEF DESCRIPTION OF THE FIGURES

FIGS. 1A–C shows the encoding part of the cDNA sequence of recombinant human prothrombin and the amino acid sequence derivable therefrom (SEQ ID NOS 7 & 8 respectively), the physiological cleavage sites for processing the protein and the cleavage sites of factor Xa, respectively, for activating the prothrombin to thrombin being entered;

FIG. 2 shows a summary of the point mutation of a preferred prothrombin derivative as compared to wt-prothrombin, the underlined amino acid/nucleotides having been exchanged;

FIG. 3A shows the flow diagram of the cloning of prothrombin-Asn419;

FIG. 3B shows a Western blot to compare plasmatic prothrombin, recombinant wt-prothrombin and prothrombin-Asn419;

DETAILED DESCRIPTION OF ASPECTS OF THE INVENTION

EXAMPLES

Figure 4:
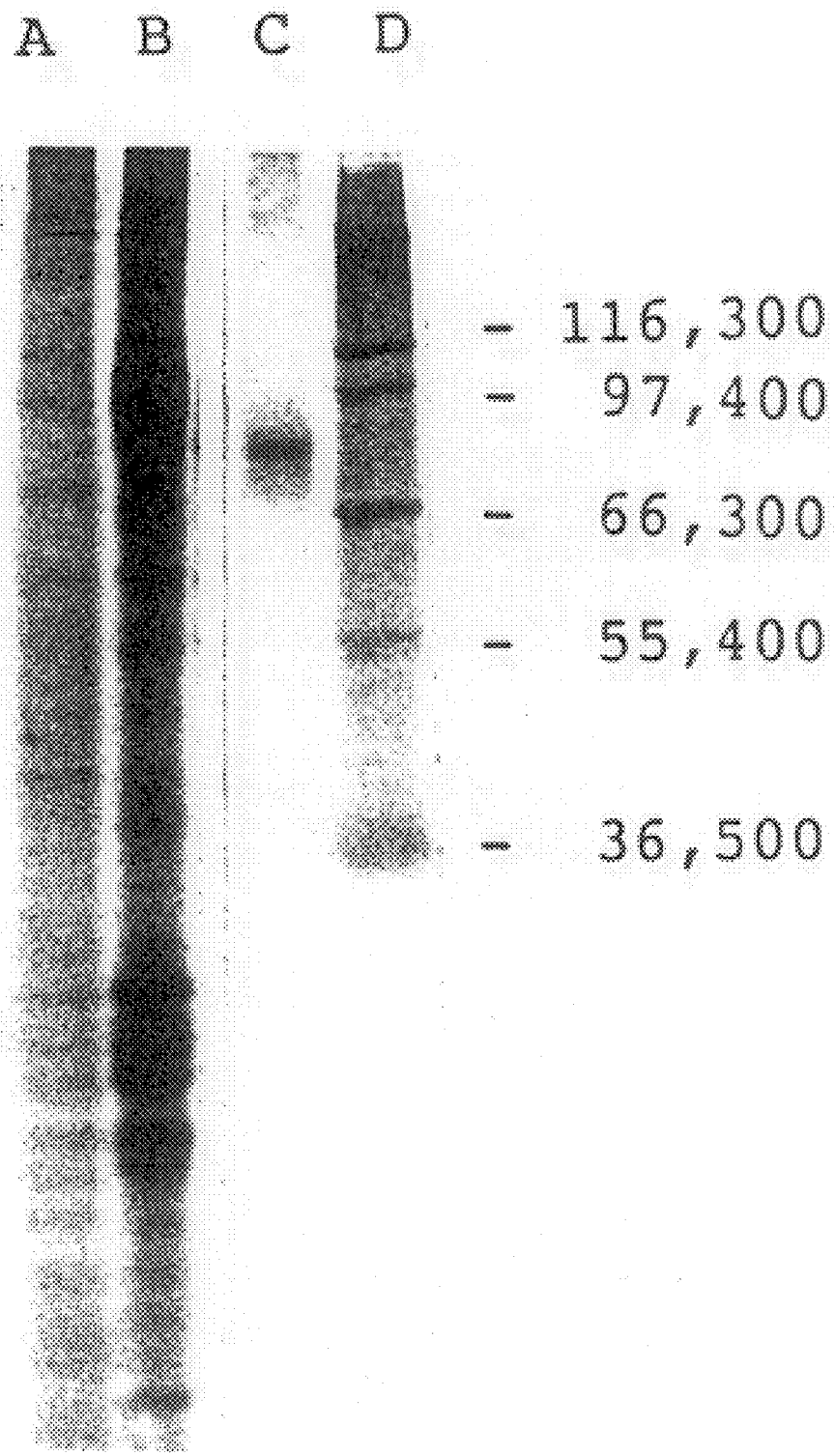
FIG. 4 represents the denaturing electrophoresis of individual purification stages of recombinant prothrombin derivatives (A: cell culture supernatant; B: eluate 3; C: eluate 4;D: molecular weight marker)

Example 1 shows the procedure by which a point-mutated prothrombin can be obtained, by way of the example prothrombin-Asn419. Example 2 demonstrates the purification and functional analysis of the prothrombin derivative. Example 3 shows the recovery and functional analysis of the thrombin derivative. Example 4 quantitates the binding acitivity of the thrombin derivative to hirudin; Example 5 checks the prothrombin derivative for its ability of acting as an antagonist of hirudin, Example 6 shows that hirudin can be neutralized by the thrombin derivative. In Example 7 it is demonstrated that the thrombin derivative is able to re-activate the thrombin from a thrombin-hirudin complex; Example 8 shows that the thrombin derivative is also effective in plasma, and Example 9 shows the recovery and functional analysis of a meizothrombin derivative.

Example 1

Construction of pSV-FIIwt and pSV-FII-Asn 419 (Asp to Asn).

Plasmid pSVβ (Nucl. Acids Res. 17: 2365; 1989) was cleaved with NotI so as to remove the internal β-galactosidase gene fragment. The remaining vector was religated and termed pSV.

To remove the largest part of the polylinker sequence located 3' to the polyadenylation site which might interfere later on, pSV was cleaved with HindIII and XbaI. After removal of the small polylinker fragment, the vector ends were filled up with Klenow enzyme and religated. The resultant plasmid was termed pSVΔ.

Subsequently, a multiple cloning site (MCS) comprising suitable restriction cleavage sites was inserted in the XhoI site located 5' of the 16/19S intron.

The MCS was chemically synthesized in the form of two complementary oligonucleotides:

5'-TCGACC<u>ATG</u>G ACAAGCTTAT CGATCCCGGG AAT-TCGGTAC CGTCGACCTG CAGGTGCACG GGC-CCAGATC TGACTGACTG A-3' (Seq.ID.No.1) and 5'-TCGATCAGTC AGTCAGATCT GGGCCCGTGC ACCTGCAGGT CGACGGTACC GAATTCCCGG GATCGATAAG CTTGTCCATG G-3' (Seq.ID.No.2)

The two oligonucleotides were annealed and inserted in pSVΔ. Since the MCS insert had XhoI-compatible, sticky ends, yet not complete XhoI-sites, the ligation reaction was cleaved with XhoI. Non-cleavable constructs represented the desired plasmid which was termed pSV-MCS III.

A DNA-fragment having the complete human wt-prothrombin-cDNA was cut out of plasmid pTKemc-PT2 (WO 91/11519) by means of partial NcoI and complete SmaI restriction digests.

This fragment was inserted in vector pSV-MCS III, after the latter had also been completely opened via partial NcoI and complete SmaI digests.

The resultant plasmid was termed pSV-FIIwt and expresses wt-prothrombin, as detected by transient expression in COS cells and stable expression in CHO cells; the sequence of the functional elements of pSV-FIIwt is SV40-promoter/enhancer (of the early genes), SV40-5' UTR, wt-prothrombin-cDNA, SV40-16s/19s intron, SV40-polyadenylation site and pUC 19-sequences (with bacterial replication origin and ampicillin resistance gene).

To mutate the aspartic acid of the catalytic center of the thrombin to an asparagin and thus prepare an inactive mutant of the thrombin, pSV-FIIwt was mutated: The codon encoding for the said aspartic acid is located on an EcoRV-DraIII restriction fragment. Both restriction sites are uniquely present in pSV-FIIwt. The intended mutagenesis was carried out by means of polmerase chain reaction with the primer pair 2104/2066 (Seq.ID.Nos. 3 and 4), whereupon the wt-prothrombin-EcoRV-DraIII fragment was substituted by the PCR Ecl136II-DraIII-fragment that contained the mutation.

The two oligonucleotides were chemically synthesized:

Primer 2104 (5'-TAACTGACGG TCCTTGAGCT CCAT-GTTGGA AAAGATCTAC ATC-3') (Seq.ID.No.3) as 5' primer; following the polymerase chain reaction, the Ecl136II half site is ligated to the EcoRV half site of the vector, by which some nucleotides of the wt-prothrombin were changed on DNA-level, yet the amino acid sequence is maintained as in wt-prothrombin.

Primer 2066 (5'-GCAGACACAC AGGGTGAATG TAGT-CACTGA AGGCAACAGG CTTCTTCAGC TTCAT-CAGGG CAATATTCCG GTCCAGGTTC TCCCGC-3') (Seq.ID.No.4) as 3' primer; by this primer, the aspartic acid is mutated to asparagine on DNA level, an SspI restriction site is introduced and an NciI site is lost.

The PC reaction was carried out under standard conditions at an annealing temperature of 55° C.

The resultant plasmid pSV-FIIAsn419 which contains the Asp→Asn mutation was identified by its restriction pattern with EcoRV, DraIII, SspI and NciI in comparison with pSV-FIIwt.

The flow diagram of the cloning route is shown in FIG. 3A.

The expected nucleotide sequence of the Ecl136II-DraIII insert in pSV-FIIAsn419 was confirmed by subsequent sequencing with the 5' and 3' primers 2197 (5'-CATAAGCCTG AAATCAACTC-3') (Seq.ID.No.5) and 2198 (5'-CTTCGGAGCG TGGAGTCATC-3') (Seq.ID.No.6), respectively.

Dihydrofolate reductase gene-deficient CHO-DUKS B11 routinely grow in complete medium (DMEM/Ham's F12 1:1 medium, supplemented with 2 mM glutamine, 0.075% bicarbonate, 100 IU penicillin and 100 mg of streptomycin/ml, 10% fetal calf serum as well as 10 mg of deoxyadenosine, adenosine and thymidine per ml).

By means of a modified $CaPO_4$ method (Graham and van der Eb, Virology 52: 456, 1973), the cells were cotransfected with 10 μg of pSV-FIIwt and pSV-FIIAsn-419, respectively, and 1 μg of pSV-dhfr (Fischer et al., FEBS Lett. 351:345, 1994): to the DNA in 250 ml of 1 mM Tris, pH 8,0, 0.1 mM EDTA, there were added 25 ml of 2.5 M $CaCl_2$. Subsequently, 250 ml of 280 mM NaCl, 45 mM Hepes, 2.8 mM $Na_2HPO_4$, pH 7.12, were added. After 10 minutes the DNA coprecipitate formed was added to the subconfluent cells.

Six hours later, the medium was sucked off, and the cells were overlaid with 15% glycerol in PBS. One minute later, the glycerol was sucked off, the cells were washed with PBS, and the cells were provided with fresh complete medium.

48 hours later, the cells were trypsinized and partitioned in various concentrations in selection medium (DMEM/F12 1:1 medium without hypoxanthine glycine and thymidine; supplemented with 2 mM glutamine, 100 IU penicillin and 100 mg of streptomycine/ml, and 10% dialysed fetal calf serum with an exclusion volume of 10,000 Kd). With a regular exchange of medium 2–3 times per week, cell clones were visible after approximately 10 days. After further week, the resultant cell clones were isolated and grown to confluence in separate cell culture dishes. In serum-free 24 hour cell culture supernatants with secreted, recombinant wt prothrombin or prothrombinAsn419, respectively, in selection medium (supplemented with 10 μg of vitamin $K_1$/ml, yet without calf serum), subsequently the antigen amount and qualitative integrity (Western blot analysis), functionality (suitable activity tests) and interaction of the prothrombin, activated to thrombin, with hirudin were examined. The cell number was determined after trypsinization of the cells in the cell counter of Schärfe, Reutlingen, Germany.

For the Western blot analysis, 10 μl of cell culture supernatant were reduced and denatured, and partitioned in denaturing 4% collecting-/8% separating gels according to L ämmli (Nature 227: pp. 680, 1970) by means of the BioRad Mini-Protean II Dual Slab Gel System (BioRad Laboratories, Richmond, Calif., U.S.A.). After the gel run had been effected, the proteins were transferred in transfer buffer (25 mM Tris, 192 mM glycine) to nitrocellulose membranes by means of the BioRad Mini Trans-Blot-System (BioRad Laboratories, Richmond, Calif., U.S.A.). The Protoblot System of Promega (Madison, Wis., U.S.A.) was used to visualize the recombinant protein. Rabbit-anti-prothrombin-serum (Lot No.A325) of Dakopatts (Glostrup, Denmark) was used as the antibody for prothrombin binding (FIG. 3B).

Example 2

Purification and Activity Determination of Recombinant Wt-Prothrombin and Prothrombin Derivatives a) Purification of the recombinant wt-prothrombin and of the prothrombin-Asn419

Material:

Anion exchange column Fraktogel EMD
TMAE 6 50, 1.6×5 cm (Merck)
Liquid chromatography apparatus FPLC LCC-500 (Pharmacia)
anti-Prothrombin-immunoglobulin (Stago)

Solutions:

50 mM Tris/HCl buffer pH 7.4 (buffer A)
50 mM Tris/HCl buffer pH 7.4, 180 mM NaCl (buffer B)
50 mM Tris/HCl buffer pH 7.4, 300 mM NaCl (buffer C)
50 mM Tris/HCl buffer pH 7.4, 160 mM NaCl,
10 mM Ca-acetate (buffer D)

For the recovery of the recombinant wt-prothrombin and of the prothrombin derivative, the cell culture supernatant of transformed CHO cells from Example 1 was used which contained a soluble recombinant prothrombin derivative.

Purification of the recombinant wt-prothrombin and of the prothrombin derivative from the cell culture supernatant was effected by liquid chromatography. During the chromatography, the course thereof was followed in the usual manner by absorption measurement at 280 nm. The content of prothrombin and of prothrombin derivatives, respectively, of the individual fractions and eluates was determined in the usual manner by means of ELISA by using a commercially common prothrombin preparation as the standard.

The total protein concentration was determined according to the method of Bradford, M. (Anal. Biochem. 72, 248 (1976).

The purification method is described in Fischer et al., J. Biotechn. 38:129, 1995.

The data relating to the purification of the wt-prothrombin are not shown.

To purify prothrombin-Asn419, the anion exchange column was equilibrated with buffer A, and subsequently 970 ml of cell culture supernatant (prothrombin content (ELISA) 20 µg/ml; protein concentration 2.7 mg/ml) were applied at a rate of 4 ml/minute. Material not bound to the exchange gel was removed by flushing the column with buffer A (eluate 1: 1030 ml: 1.2 mg/ml). Subsequently, proteins weakly bonded to the column were removed by flushing the column with buffer B (eluate 2: 20 ml; prothrombin content (ELISA) 2 µg/ml; total protein content 10.0 mg/ml). Thereafter, the column was eluted with buffer C, and protein bound to the column was obtained in the eluate (eluate 3: 30 ml; prothrombin content (ELISA) 355 µg/ml; total protein content 16 mg/ml). Subsequently, the column was regenerated by washing with 1 M NaCl solution and equilibrated with buffer D. 28 ml of eluate 3 were 1.9-fold diluted with buffer A, and Ca-acetate was added to a final concentration of 10 mM. This solution in turn was filtered through the anion exchange column and flushed with buffer D, unbound protein being obtained in the eluate (eluate 4: 60 ml; prothrombin content (ELISA) 170 µg/ml). In the individual stages of chromatography, the protein was examined by means of denaturing SDS polyacrylamide gel electrophoresis (SDS-PAGE) (Laemmli, 1970). FIG. 4 shows the purification of the prothrombin derivative by means of SDS-PAGE. From the illustration it is apparent that the prothrombin derivative in eluate 4 was obtained in pure form.

b) Activity determination of the prothrombin derivative:

All the purification stages and eluates were examined in terms of coagulation activity of prothrombin by means of prothrombin-time-test (Quick AJ, J. Biol. Chem. 109:73, 1935, and Denson KWE et al., in Laboratory Diagnosis, Blackwell R. Scientific Publications Oxford 1976, pp. 310.) Neither in the cell culture supernatant, the individual purification stages, nor in eluates 1–4 could a prothrombin activity be detected.

Example 3
Recovery, Analysis and Activity Determination of Wt-Thrombin and Thrombin-Asn99 a) Recovery of Thrombin-Asn99:

The recovery of thrombin-Asn99 was effected analogous to the method described in EP-A-0 565 512, by cleaving the prothrombin- Asn419 by means of immobilized trypsin.

Figure 5:
FIG. 5 shows the denaturing electrophoresis of individual stages of the formation of Thrombin-Asn99 from Prothrombin- Asn419 (A: Prothrombin-Asn419; B: eluate 3; C: human thrombin; D: molecular weight marker)

The eluate obtained after activation was examined by means of denaturing SDS-PAGE (FIG. 5). The results of SDS-PAGE show that recombinant prothrombin derivative has been changed into a thrombin derivative (Thrombin-Asn99) having a molecular weight of 33,000 (heavy chain).

In parallel thereto, recombinant wt-prothrombin is activated to thrombin according to the same method.

b) Analysis of the amino acid sequence of the thrombin derivative Thrombin-Asn99

N-terminal amino acid sequence analysis yielded the following two sequences (SEQ ID NOS 9 & 10): (A) Thr-Ala-Thr-Ser-Glu-Tyr-Gln-Thr-Phe-Phe-Asn-Pro-Arg-Thr-Phe; (B) Ile-Val-Glu-Ser-Asp-Glu-Ile-Gly-Met-Ser-Pro-Trp-Gln. Thus, the sequences show that the recombinant thrombin derivative was obtained by proteolysis at the authentic cleavage sites of prothrombin (Arg271-Thr272 and Arg320-Ile321) as a two-chain molecule having α-thrombin structure.

Figure 11:
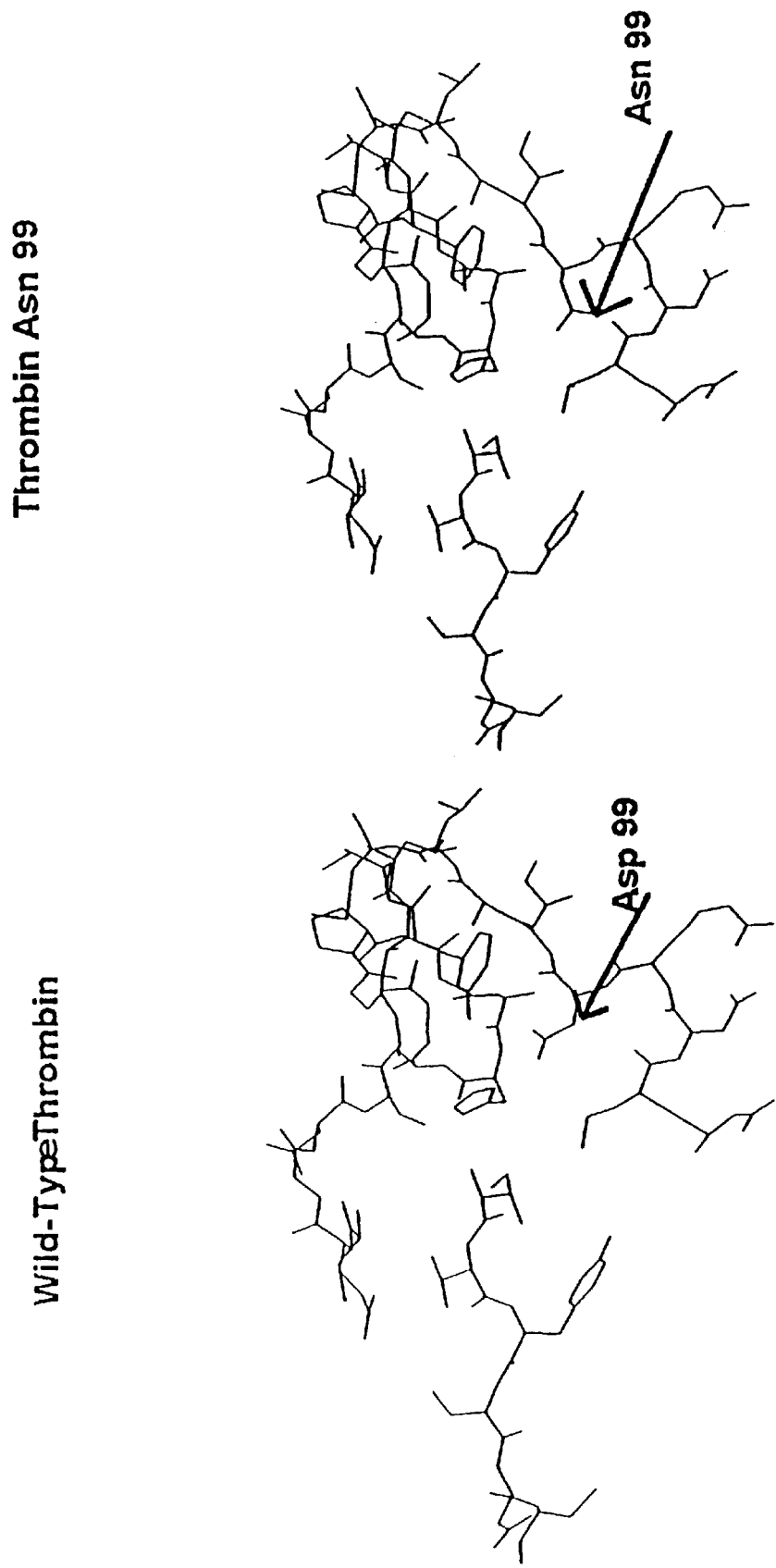
FIG. 11 represents the molecular structure of the catalytic center in the thrombin-hirudin complex (comparison of human thrombin and recombinant thrombin derivative), the structural changes caused by the mutation Asp→Asn being indicated by arrows, and Ser, His and Asp or Asn, respectively, representing the position of the amino acids of the catalytic center in the thrombin molecule and Ile representing the N-terminal amino acid of hirudin.

To better illustrate the spacial structure of the thrombin-Asn99-hirudin complex, FIG. 11 shows the molecular structure of the catalytic center. FIG. 11 shows the comparison between human thrombin and the recombinant thrombin derivative Asn99.

c) Activity determination of the recombinant Thrombin-Asn99 was effected according to three independent methods.

I. Determination of the Thrombin Activity by Means of Chromogenic Substrate

The determination of the thrombin activity by means of chromogenic substrate was effected at 25° C. in 50 mM Tris/HCl buffer, 150 mM NaCl, 0.1% PEG 6000, pH 8.0, at a concentration of the synthetic chromogenic substrate of 0.2 mM AcOH-DH-CHG-Ala-Arg-pNA (TH-1, Pentapharm) in a volume of 1 ml. The absorption at 410 nm was determined in dependence on time. Thrombin standard of a defined activity (Immuno AG) was used as reference. The dilutions of the samples in the test buffer were effected with an addition of 1% Prionex (collagen hydrolysate, Pentapharm).

The activity determination gave an activity of 0.24 nmol/min µg protein for the recombinant thrombin derivative Thrombin-Asn99. Thus, Thrombin-Asn99 has an activity of merely 0.24% in the chromogenic assay as compared to human plasmatic thrombin.

TABLE 1

Determination of thrombin activity by means of chromogenic substrate

| Thrombin Derivative | Specific Activity (nmol/min µg protein) |
| --- | --- |
| Thrombin-Asn 99 | 0.24 |
| Recombinant wt-thrombin | 98.4 |
| Human plasmatic thrombin | 102.0 |

II. Determination of the Activity by Using a Thrombin Standard

All the thrombin derivatives were assayed for their thrombin activity by using a thrombin standard (Immuno AG) of defined activity. In this activity determination, no activity was found for Thrombin-Asn99 (Table 2).

TABLE 2

Determination of activity by using a thrombin standard

| Thrombin Derivative | Activity (IU/mg protein) |
| --- | --- |
| Thrombin-Asn99 | 0 |
| Recombinant wt-thrombin | 1656 |
| Human plasmatic thrombin | 1509.0 |

III. Activity Determination by Titration of the Active Site

Titration of the active site of the thrombin derivatives was effected according to the method of M. F. Doyle and P. E. Haley (Methods in Enzymology (1993), 222, 299–312), by using p-nitrophenyl-p'-guanidino-benzoate as substrate and an extinction coefficient of 16,595 $M^{-1}$ $cm^{-1}$ at 410 nm.

Human plasmatic thrombin, recombinant wt-thrombin and Thrombin-Asn99 were assayed for their content at the active site (active thrombin concentration) by means of this method. With this, no active site could be found for Thrombin-Asn99 (Table 3).

TABLE 3

Activity determination by titration of the active site

| Thrombin Derivative | Concentration of Active Thrombin (nmol/mg protein) |
|---|---|
| Thrombin-Asn99 | 0 |
| Recombinant wt-thrombin | 16.34 |
| Human plasmatic thrombin | 16.89 |

Conclusion: In contrast to recombinant wt-thrombin and human plasmatic thrombin, Thrombin-Asn99 exhibits an extremely low thrombin activity in merely one of three test methods, corresponding to approximately 1/400 of the native thrombin activity. Recombinant wt-thrombin and human plasmatic thrombin exhibit very similar activity patterns.

Example 4
Quantitation of Hirudin Binding of the Recombinant Thrombin Derivative I. The binding capacity to hirudin of the thrombin derivative Thrombin-Asn99 was examined by means of an ELISA assay and compared with human plasmatic thrombin and recombinant wt-thrombin. This ELISA assay is based on the use of immobilized hirudin. According to one of the embodiments of this assay, thrombin is bound to hirudin which has been immobilized on microtiter plates and is detected via antibodies with subsequent colour reaction. This assay is independent of the enzymatic activity of the thrombin.

Figure 6:
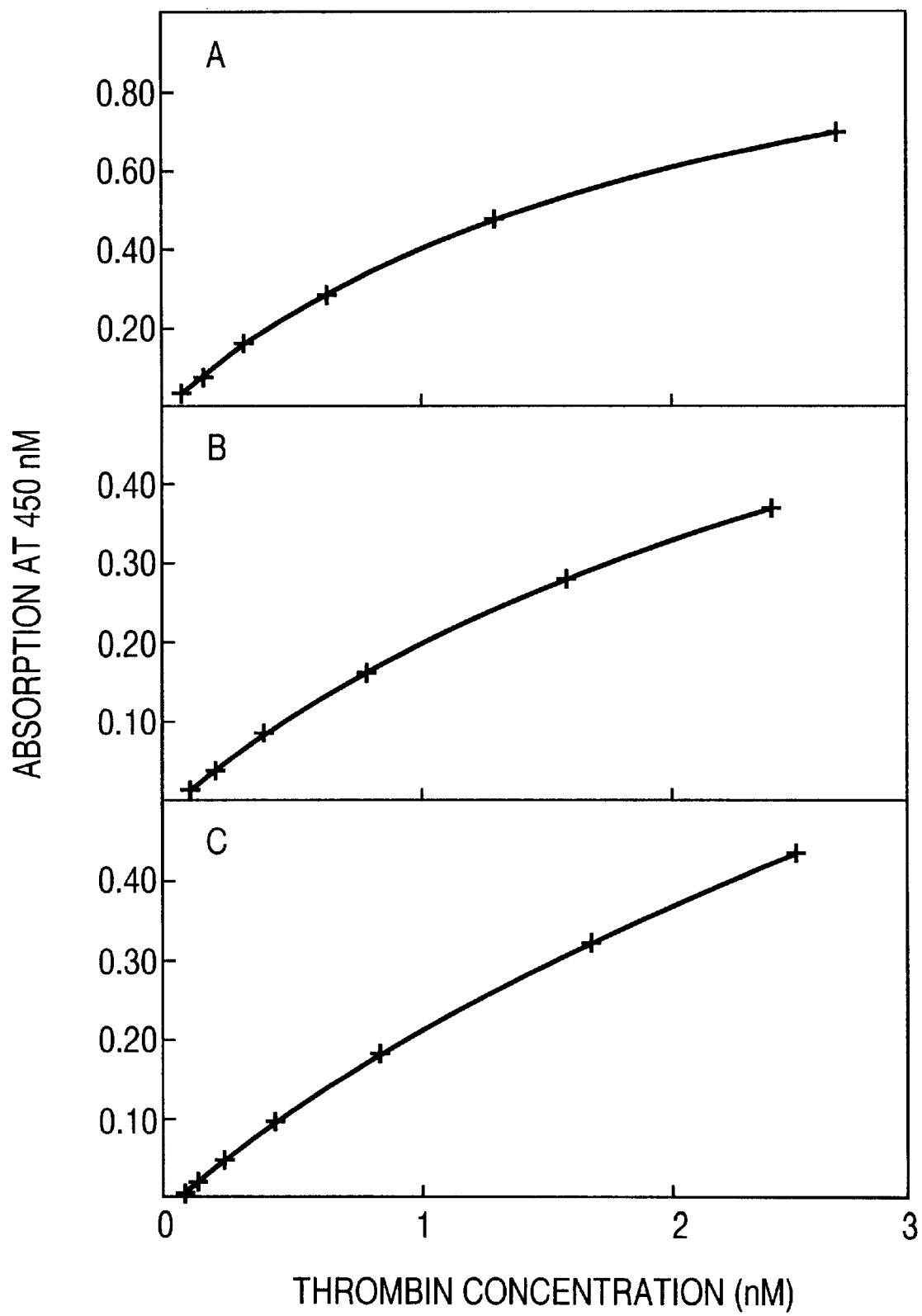
FIG. 6 shows the binding of Thrombin-Asn99 (A), recombinant wt-thrombin (B) and human plasmatic thrombin (C) to immobilized hirudin.

To prepare the ELISA plates, recombinant hirudin, variant 1 (Variante 1; Rhein Biotech, FRG; 2 µg/ml, 100 µl) is bound to microtitration plates. After washing, recombinant wt-thrombin, thrombin Asn99 or human plasmatic thrombin (100 µl of a solution at the concentrations according to FIG. 6) is added and incubated for one hour. Non-bound thrombin was removed, and bound thrombin was detected by means of peroxidase-labelled anti-thrombin-immunoglobulin (Sheep anti-human Thrombin; Enzyme Research Lab. Inc., Indiana, U.S.A.; 100 µl of a ⅟1000) (FIG. 6). Absorption measurement was effected at 450 nm.

From the results it is clearly apparent that recombinant wt-thrombin (FIG. 6B), human plasmatic thrombin (FIG. 6C), as well as thrombin-Asn99 (FIG. 6A) bind to immobilized hirudin in identical and concentration-dependent manner.

II. Determination of the binding of hirudin to thrombin by changing the fluorescence of aromatic amino acids in the thrombin molecule and determination of the binding constant of hirudin to thrombin derivatives.

By way of fluorescence emissions, using the PC program ENZFITTER (RJ. Leatherbarrow, Elsevier-Biosoft, 1987) and by using a binding model with a mutual binding site as a basis, the binding constant of thrombin to hirudin was determined. The determination of the intrinsic fluorescence of aromatic amino acids of the thrombin derivatives was effected in 50 mM Tris/HCl buffer, 150 mM NaCl, 0.1% PEG 6000, pH 7.4. Excitation occurred at 280 nm (gap width 2.5 nm), the emission was registered between 300 nm and 400 nm (gap width 5 nm).

The intrinsic fluorescence of tryptophane in the thrombin molecule was excited at 280 nm, and the emission between 300 nm and 400 nm was measured without the addition of hirudin and in the presence of hirudin, respectively. The fluorescence at 341 nm (excitation 280 nm) of 390 nM thrombin-Asn99, 326 nM recombinant wt-thrombin and 350 nM human plasmatic thrombin was determined in dependence on the hirudin concentration.

Figure 7:
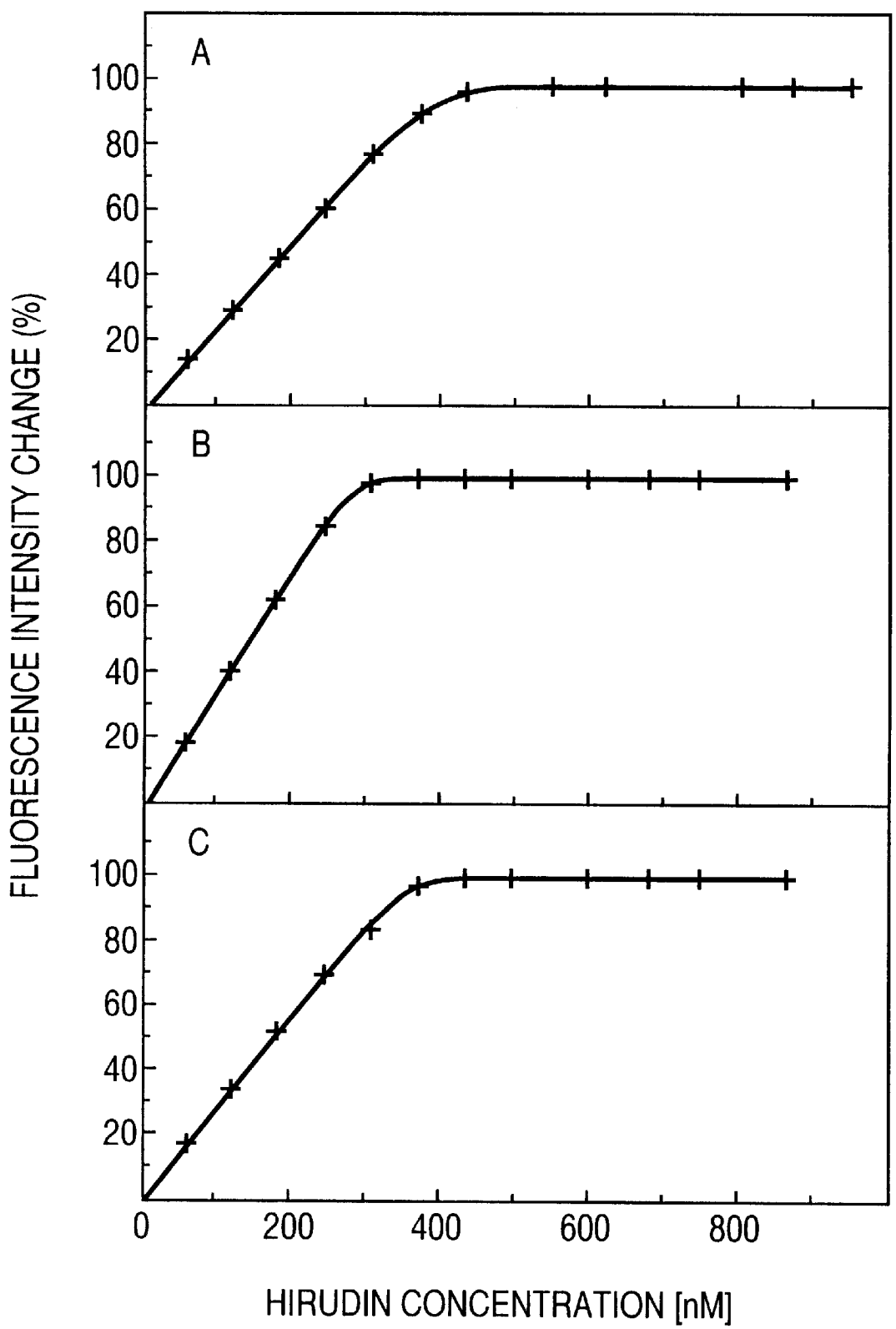
FIG. 7 indicates the dependence of the thrombin fluorescence on the hirudin concentration (the fluorescence at 341 nm (excitation 280 nm) of 390 mM Thrombin-Asn99 (A), 326 nM recombinant wt-thrombin (B) and 350 nM human plasmatic thrombin (C) were determined in dependence on the hirudin concentration, the fluorescence without hirudin being illustrated as 0%, the fluorescence at hirudin saturation as 100%)

Again, the thrombin derivative Thrombin-Asn99 is compared with recombinant wt-thrombin and human plasmatic thrombin. From the results it is apparent that in presence of hirudin, the fluorescence of tryptophane in the thrombin molecule (hirudin has no tryptophane) increases substantially relative to all three thrombin derivatives (FIG. 7). Apparently this is due to the formation of a hirudin-thrombin complex.

Apparently this leads to a structural change in the thrombin molecule which influences the fluorescence properties of tryptophane. From spacial structural analyses of the thrombin-hirudin complex it is known that particularly Trp 51, Trp 148 and Trp 227 from thrombin as a consequence of hirudin binding get into contact vicinity to the inhibitor.

By way of comparison, FIG. 7 shows the dependence of the thrombin fluorescence on the hirudin concentration. For all three thrombin derivatives, very similar bindings of hirudin to thrombin were obtained. The binding of hirudin to all three thrombin derivatives corresponds to a saturation and results in one binding site per thrombin molecule.

The data of FIG. 7 were used to determine the binding constants of hirudin on the thrombin derivatives (Table 4). It is apparent that very similar and very high association constants were obtained for all thrombin derivatives.

TABLE 4

Binding constants of hirudin to the thrombin derivatives

| Thrombin Derivative | Association Constant of the Thrombin-Hirudin-Complex ($M^{-1}$) |
|---|---|
| Thrombin-Asn99 | $3.7 \times 10^7$ |
| Recombinant wt-thrombin | $4.3 \times 10^7$ |
| Human plasmatic thrombin | $3.2 \times 10^7$ |

Example 5
Recombinant Prothrombin as Hirudin-Antagonist

Material: Coagulometer KC 10 (Amelungen GmbH, Germany) Prothrombin-free normal plasma (Immuno AG, Vienna) Prothrombin concentration standard (Immuno AG, Vienna) Recombinant hirudin (Rhein Biotech, Germany).

In a common laboratory method, the time required after activation of the factors participating in blood coagulation to make normal plasma coagulate was determined by means of a prothrombin-time-assay. By the addition of $Ca^{2+}$ ions to the mixture of 1. prothrombin-free normal plasma (which, however, contains all the other coagulation factors), and 2. prothrombin concentration standard (prothrombin having a defined activity), in this assay coagulation factor Xa is formed which then converts prothrombin (factor II) into thrombin (factor IIa). Thrombin then causes the conversion of soluble fibrinogen into insoluble fibrin. This leads to the formation of blood clots. The time interval between activation by the addition of the $Ca^{2+}$ ions and the formation of the blood clot is automatically determined by means of the coagulometer. As is known, the duration of blood coagulation depends on the concentration of the prothrombin or on the concentration of the active thrombin formed, respectively. The higher the thrombin concentration in the reaction mixture, the lower the clotting time. With the addition of a thrombin inhibitor, such as hirudin, an inactive thrombin-hirudin complex forms after the conversion of prothrombin to thrombin, so that in thrombin bound in this complex can no longer participate in the conversion of fibrinogen to fibrin. As a consequence, the clotting time increases on account of the reduced amount of active thrombin. With an excess of inhibitor as compared to thrombin, there results a complete inhibition of blood coagulation. If however, both, a thrombin inhibitor, such as hirudin, and a further component which in turn binds the inhibitor but does not participate in blood coagulation are added in an assay system, the effect of the inhibitor on thrombin decreases. Then the clotting time is shortened again. In Table 5, the results of various examinations are summarized:

From the results of Table 5 there follows:
1. Prothrombin leads to a rapid formation of the blood clot.
2. Hirudin leads to an inhibition of blood coagulation.
3. The recombinant prothrombin derivative does not lead to blood coagulation.
4. The recombinant prothrombin derivative does not affect the blood coagulation by natural prothrombin.
5. By the addition of recombinant prothrombin derivative, the hirudin-dependent inhibition of blood coagulation is cancelled out.

TABLE 5

| Components in the Coagulation Assay | Clotting Time (s) |
|---|---|
| Formulation (A) | 18 |
| Prothrombin-free normal plasma | |
| 125 mU/ml (12.5 µg/ml) prothrombin | |
| Formulation (B) | >100 |
| Prothrombin-free normal plasma | |
| 125 mU/ml (12.5 µg/ml) prothrombin | |
| 2.5 µg/ml hirudin | |
| Formulation (C) | >100 |
| Prothrombin-free normal plasma | |
| 25 µg/ml prothrombin derivative | |
| according to the invention | |
| Formulation (D) | 18 |
| Prothrombin-free normal plasma | |
| 125 mU/ml (12.5 µg/ml) prothrombin | |
| 25 µg/ml prothrombin derivative | |
| according to the invention | |
| Formulation (E) | 35 |
| Prothrombin-free normal plasma | |
| 125 mU/ml (12.5 µg/ml) prothrombin | |
| 25 µg/ml prothrombin derivative | |
| according to the invention, 2.5 µg/ml hirudin | |

Example 6
Neutralization of Hirudin by Thrombin-Asn99

Figure 8:
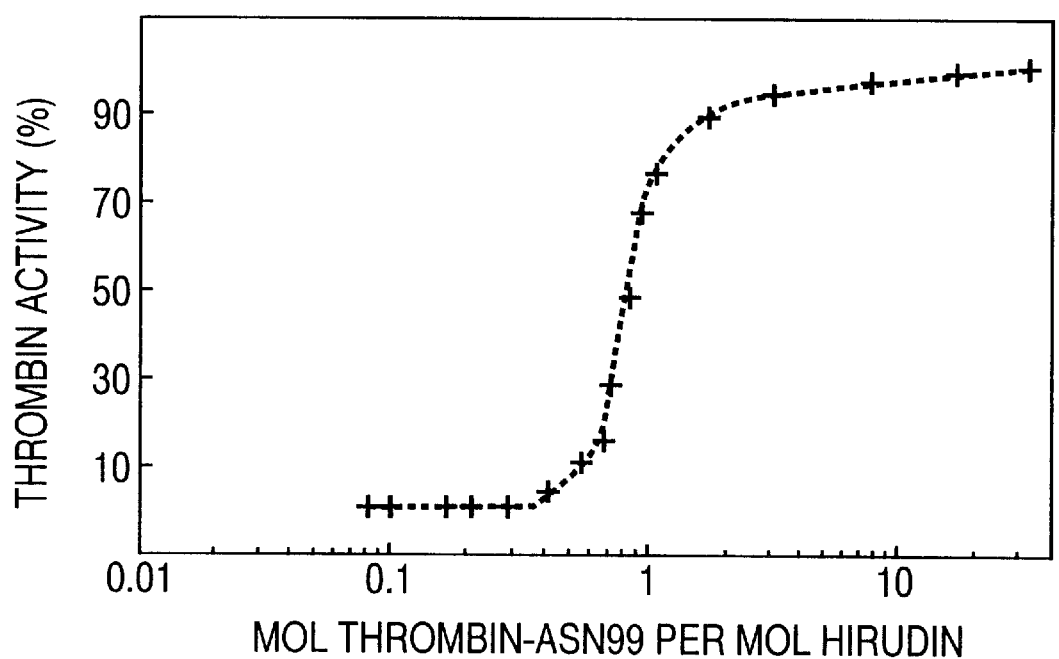
FIG. 8 shows the neutralization of hirudin by Thrombin-Asn99.

To test whether or not Thrombin-Asn99 is able to neutralize hirudin and thus the inhibition relative to active thrombin is cancelled out, 50 µl of hirudin (44 nM, 4 ATU/ml) having various concentrations of thrombin-Asn99 were incubated for 1 minute. Subsequently, 50 µl of thrombin standard (3.9 IU/ml) as well as a chromogenic substrate were added in measuring buffer (0.2 mM substrate according to Example 3c in 50 mM Tris/HCl buffer, 150 mM NaCl, 0.1% PEG 6000, pH 8.0), and the enzymatic activity was determined at 25° C. The thrombin activity was photometrically determined at 410 nm. For reasons of comparison, the thrombin activity without hirudin (100% thrombin activity), as well as the thrombin activity in the presence of hirudin, yet without the addition of Thrombin-Asn99 (0% thrombin activity) were determined. The results are illustrated in FIG. 8.

It is clearly apparent that hirudin is neutralized by Thrombin-Asn99, and thus the inhibiting effect of hirudin on active thrombin is cancelled out. Simultaneously it becomes clear that at a ratio of 1 mol Thrombin-Asn99 to 1 mol hirudin, the thrombin inhibition is neutralized.

Example 7
Reactivation of the Thrombin-Hirudin Complex by Thrombin-Asn99

The experiment was aimed at determining whether or not the thrombin activity can be re-attained by the addition of Thrombin-Asn99 to the thrombin-hirudin complex, i.e. whether or not Thrombin-Asn99 is capable of neutralizing hirudin from the thrombin-hirudin complex.

For this, the activity of thrombin (final concentration 0.1 IU/ml) was continuously photometrically determined by means of chromogenic substrate. After 3 minutes, hirudin (final concentration 0.1 ATU/ml) was added, and the reaction was continued for further 4 minutes. Then different concentrations of Thrombin-Asn99 (final concentrations 0.2 µg/ml, 0.4 µg/ml and 1 µg/ml) were added, and the reaction was followed photometrically (FIG. 6).

Figure 9:
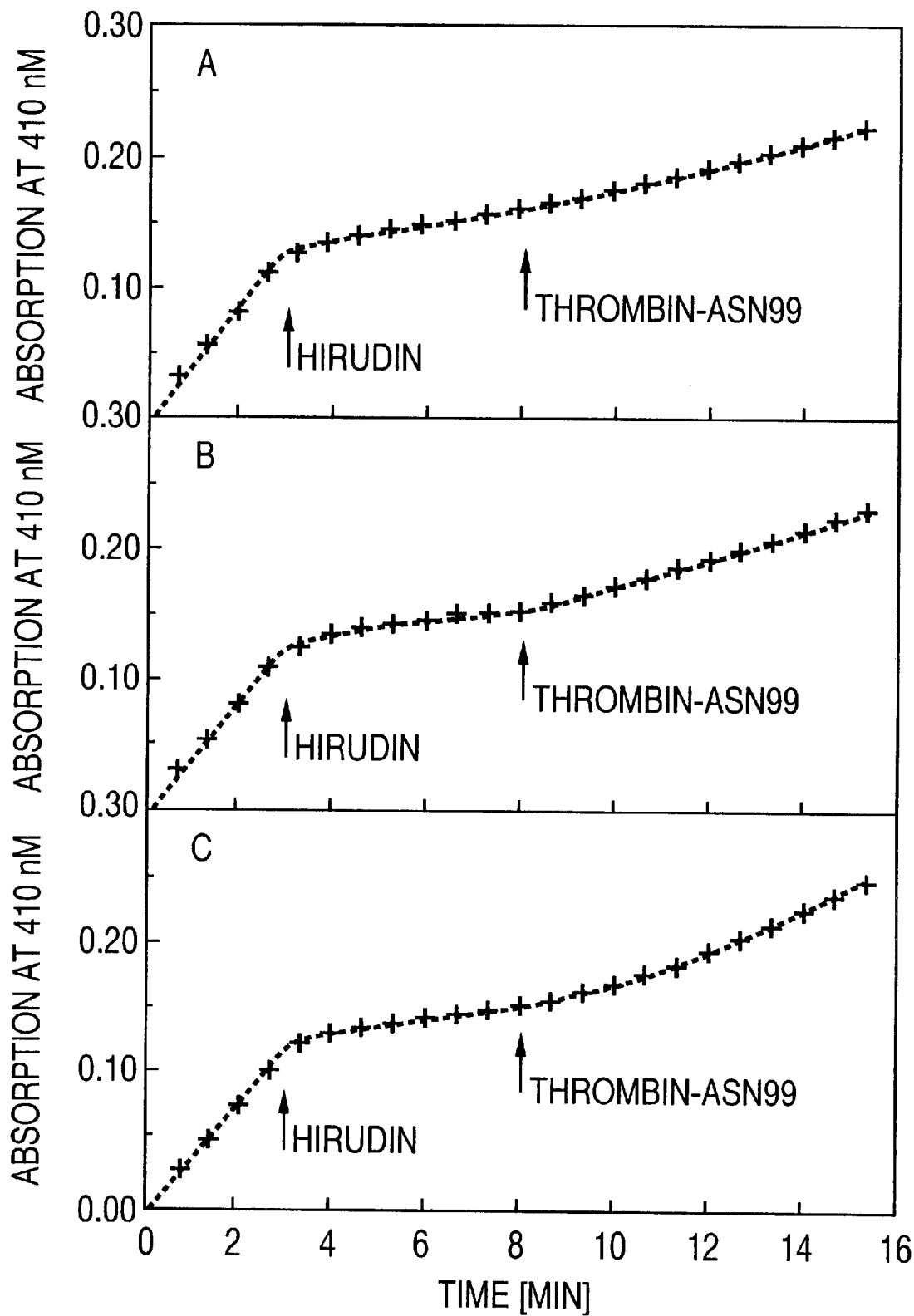
FIG. 9 shows the reconstitution of the thrombin activity from the hirudin-thrombin complex by the addition of Thrombin-Asn99 with different concentrations of Thrombin-Asn99: (A) 0.2 µg/ml, (B) 0.4 µg/ml, (C) 1 µg/ml.

FIG. 9 shows that by the addition of hirudin to thrombin, the activity of the latter is inhibited. From the results it is furthermore apparent that by the addition of increasing concentrations of thrombin-Asn99, it is, however, possible to cancel out again the inhibitory action of hirudin on thrombin.

What is interesting is that the process of hirudin neutralization is time-dependent; it takes approximately 1 minute for hirudin to become neutralized by Thrombin-Asn99. This is due to the very high binding constant of hirudin to thrombin, whose balance consequently is shifted time-dependent in favour of free thrombin and the formation of a hirudin-Thrombin-Asn99 complex.

Example 8
Neutralization of Hirudin in Plasma

Figure 10:
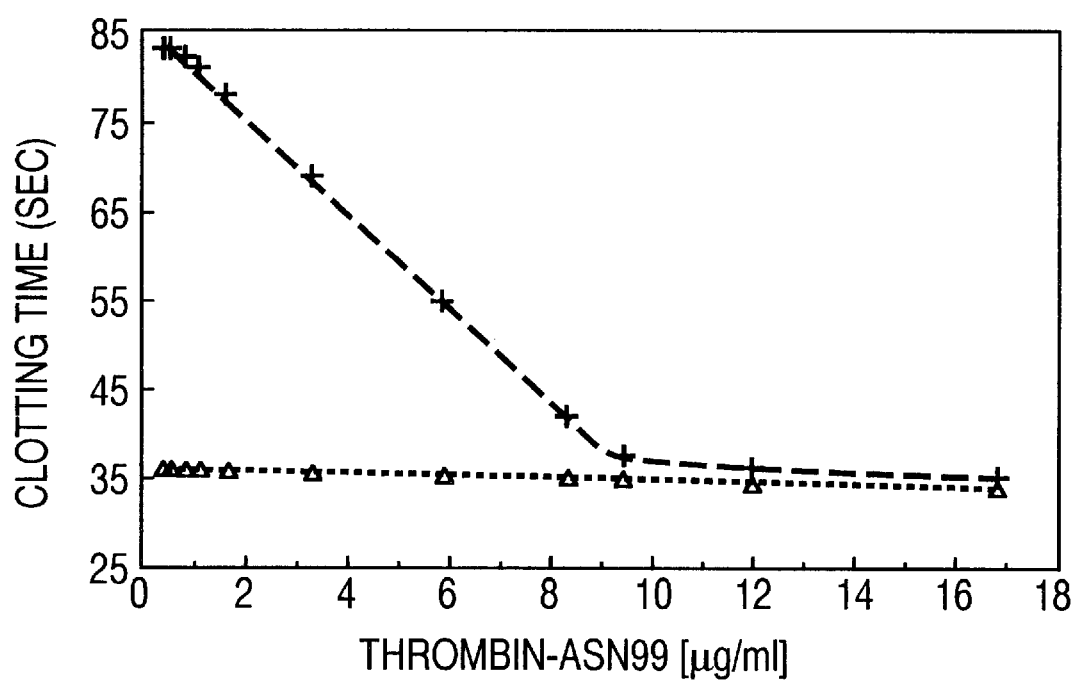
FIG. 10 shows the neutralization of hirudin in plasma (the clotting time in the presence of hirudin (x---x) and without the addition of hirudin (......) being illustrated in the test in dependence on the concentration of Thrombin-Asn99)

The examination was aimed at showing that Thrombin-Asn99 is capable of neutralizing hirudin in plasma, too, and thus of cancelling out an inhibiting effect of hirudin on thrombin. For the realization thereof, analogous to the aPPT-test, 110 µl of hirudinized citrated plasma (hirudin concentration 1.8 µg/ml) were mixed with 100 µl of partial thromboplastin reagent (Boehringer Mannheim, FRG) and 10 µl of Thrombin-Asn99 (from 0–17 µg/ml according to FIG. 10) and incubated for 3 minutes at 37° C. Subsequently, 100 µl 25 mM CaCl$_2$ were added, and the clotting time was determined automatically (FIG. 10).

From the results it is apparent that the clotting time is greatly increased by hirudin (without the addition of Thrombin-Asn99). Depending on the concentration, the clotting time decreases, however, with an increasing amount of Thrombin-Asn99 and reaches the values common for normal plasma.

From the illustration it appears clearly that hirudin is neutralized by Thrombin-Asn99 also in plasma, and thus the inhibition of hirudin on plasmatic thrombin is cancelled out.

In sum, the examination results show unambiguously that the thrombin mutant prepared, Thrombin-Asn99, according to the set aim merely has a negligibly low activity (less than 0.24% of active thrombin), but binds hirudin in an identical manner.

The property of binding hirudin enables the recombinant molecule to neutralize the inhibitor both, in the defined buffer system and in plasma. Moreover, Thrombin-Asn99 is capable of displacing hirudin from the thrombin-hirudin complex and to neutralize it.

Example 9
Recovery and Functional Analysis of Meizothrombin-Asn419

Prothrombin-Asn 419 of Example 1 was used for the recovery of recombinant meizothrombin-Asn419. Prothrombin-Asn419 was converted to meizothrombin-Asn419 by incubation with the venom-protease ecarin. There, prothrombin-Asn419 at 0.2 mg/ml in 20 mM Tris/HCl buffer, pH 7.4, 150 mM NaCl, 5 mM $CaCl_2$, was dissolved and 20 ng of ecarin (product of Pentapharm) were added to each 1 µg prothrombin-Asn419. Activation was effected at 4° C. for 4 hours. The resultant meizothrombin-Asn419 was purified and isolated analogous to the purification of Thrombin-Asn99 (Example 3) by affinity chromatography on the peptide-gel.

Meizothrombin-Asn419 prepared in this manner has the identical molecular weight of Prothrombin-Asn419 of 72,000 and consists of the Prothrombin-F1/F2/A chain (molecular weight 52,000, N-terminal amino acid sequence (amino acids 1–7 of SEQ ID NOS 7–8) Ala-Asn-Thr-Phe-Leu-Gla-Gla-) and the B-chain (molecular weight 32,000, N-terminal amino acid sequence (SEQ ID NO: 11) Ile-Val-Glu-Ser-Asp-Ala-Glu-Ile).

Analogous to the Examples 3(c)I to III, the enzymatic properties of Meizothrombin-Asn419 were assayed. In none of the test methods an activity was determined for Meizothrombin-Asn419.

Analogous to Example 4(I) and (II) it could be found out that Meizothrombin-Asn419 binds to immobilized hirudin in a concentration-dependent manner and with a strength comparable to human plasmatic thrombin and that the fluorescence intensity of aromatic amino acids increases by the binding to hirudin, as described for Thrombin-Asn99.

Analogous to Example 6 it could be demonstrated for Meizothrombin-Asn419 that it neutralizes hirudin and thus cancels out the inhibition relative to thrombin. At a ratio of 1 mol of Meizothrombin-Asn419 to 1 mol of hirudin, the thrombin inhibition is neutralized.

Analogous to Example 7, it could be demonstrated for Meizothrombin-Asn419 that hirudin can be displaced again from the complex by the addition of Meizothrombin-Asn419 to the thrombin-hirudin-complex, and thus the thrombin recovers its acitivity. The data obtained therein correspond to those of Thrombin-Asn99.

Analogous to Example 8 it could be demonstrated for Meizothrombin-Asn419 that it is capable to neutralize hirudin in plasma and thus cancel out the inhibitory action of thrombin. The data obtained therein correspond to those of Thrombin-Asn99.

Example 10
Characterization of Thrombin-Asn99 and Meizothrombin-Asn99 In Vivo The hirudin-neutralizing effects of Thrombin-Asn99 and Meizothrombin-Asn99 were assayed in an animal model: 3 min after an intravenous administration of a hirudin dose of 0.5 mg per kg body weight (200 µl) or of 200 µl of saline solution to NMRI mice (20 g body weight; each test group comprised 10 mice), 2.5 mg of Thrombin-Asn99/kg body weight and 5.0 mg of Meizothrombin-Asn99 (200 µl each) were injected. After further 3 minutes, blood was taken from the anaesthesized mice by cardiopuncture. The citrated plasma obtained was assayed for partial thromboplastin time (PTT), thrombin time (TT), anti-thrombin potential (aPT) and plasma concentration of Thrombin-Asn99 and Meizothrombin-Asn99, each measurement being carried out in triplicate.

To measure the PTT, 50 µl of citrated mouse plasma were mixed with 50 µl of factor II-deficient citrated plasma and 100 µl of partial thromboplastin reagent at 37° C. for 3 minutes. Coagulation was started by the addition of 100 µl 25 mM $CaCl_2$. To measure the TT, 50 µl of citrated mouse plasma were mixed with 150 µl of factor II-deficient citrated plasma at 37° C. for 1 minute. Coagulation was started by the addition of 100 µl of thrombin-standard (7 units/ml).

To determine the aPT, the TT of all mice of groups 1 to 8 were compared with a calibration curve of the clotting times of various thrombin standard concentrations (1 unit/ml to 10 units/ml), from which there resulted the effective thrombin concentration in the individual TT tests. The resulting differences in the effective thrombin concentration in the tests with the mouse plasma of test groups 1 and 5 to the effective thrombin concentrations in the tests with the mouse plasma of test groups 2 to 4 and 6 to 8, respectively, resulted in the anti-thrombin potential, a difference in 1 thrombin unit/ml being defined as one anti-thrombin unit.

The plasma concentrations of Thrombin-Asn99 and Meizothrombin-Asn 99 were determined by the addition of serial plasma dilutions to immobilized hirudin, Thrombin-Asn99 and Meizothrombin-Asn99 being detected by means of sheep-anti-thrombin-IgG-peroxidase conjugate. For an analysis, calibration straight lines were established by means of Thrombin-Asn99 and Meizothrombin-Asn99 concentrations of 3 ng/ml to 100 ng/ml.

The results of these assays are illustrated in Table 6.

TABLE 6

| Parameter | Thrombin-Asn99 Test Group | | | | Meizothrombin-Asn99 Test Group | | | |
|---|---|---|---|---|---|---|---|---|
| | 1 | 2 | 3 | 4 | 5 | 6 | 7 | 8 |
| PTT (sec) | 23.8 | 42.3 | 24.0 | 26.2 | 22.4 | 38.2 | 21.0 | 21.8 |
| TT (sec) | 11.4 | 19.8 | 11.6 | 11.7 | 11.6 | 19.3 | 11.2 | 12.0 |
| aTP (ATU) | 0 | 4.3 | 0 | 0.33 | 0 | 3.8 | 0 | 0.12 |
| Plasma concentration | 0 | 0 | 16 | 10 | 0 | 0 | 39 | 16 |

These data illustrate that the injection of hirudin (test groups 2 and 6) caused an increase of the PTT of at least 75%, and increase of the TT of at least 60%, the occurrence of a high aPT and no detection of thrombin in plasma.

The sole administration of Thrombin-Asn99 (test group 3) and Meizothrombin-Asn99 (test group 7) did not show any significant change of the coagulation parameters, when compared with the test groups 1 and 5, respectively, yet both proteins could be detected in mouse plasma.

The injection of hirudin followed by Thrombin-Asn99 (test group 4), and the injection of hirudin followed by Meizothrombin-Asn99 (test group 8) resulted in a normalization of the PTT and the TT, the aPT being markedly reduced. Thus, both proteins apparently were able to neutralize hirudin in circulation and thus reduce the free hirudin concentration.

Hirudin-complexed forms of Thrombin-Asn99 and Meizothrombin-Asn99 are less reactive relative to immobilized hirudin, and therefore lower concentrations of Thrombin-Asn99 and Meizothrombin-Asn99 were found in the plasma.

What is claimed is:

1. A prothrombin mutant having a binding capacity to hirudin, heparin and antithrombin III, wherein the mutant or derivative (i) has at least one amino acid selected from the group consisting of Asp-419 and His-363 based on the amino acid numbering in prothrombin according to SEQ ID NO: 8 replaced or deleted without substantially affecting binding capacity, and (ii) has an activity of no more than 0.25% of thrombin.

2. A prothrombin mutant according to claim 1, wherein the mutant has an in vivo half-life of at least one hour.

3. A prothrombin mutant according to claim 1, wherein the mutant has an in vivo half-life of no more than 10 minutes.

4. A meizothrombin mutant having an active site and a binding capacity to specific ligands and receptors, wherein said meizothrombin mutant has (i) a protein sequence wherein at least one amino acid selected from the group consisting of Cys-293, His-363, Asp-419 and Cys-439 based on the amino acid numbering in prothrombin according to SEQ ID NO: 8 has been replaced or deleted, and (ii) an activity of no more than 0.25% of thrombin, wherein said replacement or deletion of said amino acid does not affect said binding capacity.

5. A meizothrombin mutant according to claim 4, wherein at least one of Cys-293 and Cys-439 based on the amino acid numbering in prothrombin according to SEQ ID NO: 8 is replaced.

6. A meizothrombin mutant according to claim 4, wherein amino acid Asp-419 based on the amino acid numbering in prothrombin according to SEQ ID NO: 8 is replaced.

7. A meizothrombin mutant according to claim 5, wherein amino acid Asp-419 based on the amino acid numbering in prothrombin according to SEQ ID NO: 8 is replaced with Asn.

8. A pharmaceutical preparation comprising (A) a prothrombin mutant that has (i) a binding capacity to hirudin, heparin and antithrombin III, (ii) a peptide sequence wherein at least one amino acid selected from the group consisting of His-363 and Asp-419 based on the amino acid numbering in prothrombin according to SEQ ID NO: 8 has been replaced or deleted, and (iii) an activity of no more than 0.25% of thrombin, wherein said replacement or deletion of said amino acid does not affect said binding capacity, and (B) a physiologically acceptable carrier.

9. A pharmaceutical preparation according to claim 8, wherein said prothrombin mutant has replaced at least one of Cys-293 and Cys-439 based on the amino acid numbering in prothrombin according to SEQ ID NO: 8.

10. A pharmaceutical preparation according to claim 8, wherein the preparation is free from viral contaminations and DNA from the expression cell line as determinable by PCR.

11. A method for preventing the side effects associated with an anticoagulant treatment with at least one of hirudin, heparin, antithrombin III and derivatives thereof in a patient, said method comprising administering to said patient an effective dose of a medicament comprising a prothrombin mutant, wherein said prothrombin mutant has a binding capacity to hirudin, heparin and antithrombin III and has a peptide sequence wherein (i) at least one amino acid selected from the group consisting of His-363 and Asp-419 based on the amino acid numbering in prothrombin according to SEQ ID NO: 8 has been replaced or deleted, and (ii) an activity of no more than 0.25% of thrombin, wherein said replacement or deletion of said amino acid substantially does not affect said binding capacity.

12. A method according to claim 11, wherein said prothrombin mutant further comprises an amino acid replacement or deletion of at least one of Cys-293 and Cys-439 based on the amino acid numbering in prothrombin according to SEQ ID NO: 8.

13. A method for obtaining an antagonistic effect relative to a thrombin inhibitor in a patient, the method comprises administering to said patient an effective amount of a prothrombin mutant having a peptide sequence wherein (i) at least one amino acid selected from the group consisting of His-363 and Asp-419 based on the amino acid numbering in prothrombin according to SEQ ID NO: 8 has been replaced or deleted, (ii) said prothrombin mutant has a binding capacity to hirudin, heparin and antithrombin III, and (iii) an activity of no more than 0.25% of thrombin, wherein said replacement or deletion of said amino acid substantially does not affect said binding capacity.

14. A method according to claim 13, wherein said thrombin inhibitor is a natural thrombin inhibitor.

15. A method according to claim 13, wherein said thrombin inhibitor is a synthetic thrombin inhibitor.

16. A method according to claim 13, wherein said thrombin inhibitor is selected from the group consisting of hirudin, heparin, antithrombin III and derivatives thereof.

17. A method according to claim 13, further comprising changing at least one of amino acids Cys-293 and Cys-439, based on the amino acid numbering in prothrombin according to SEQ ID NO: 8 in said prothrombin mutant.

18. A prothrombin mutant or derivative according to claim 1, wherein at least one amino acid selected from the group consisting of Cys-293 and Cys-439 based on the amino acid numbering in prothrombin according to SEQ ID NO: 8 also is replaced or deleted without substantially affecting binding capacity.

19. A prothrombin mutant or a derivative thereof according to claim 1, wherein said amino acid Asp-419 has been replaced with Asn.

20. A method of inhibiting coagulation in a patient, comprising, administering to the patient a prothrombin mutant having a binding capacity to hirudin, heparin and antithrombin III, wherein the mutant (i) has at least one amino acid selected from the group consisting of Asp-419 and His-363 based on the amino acid numbering in prothrombin according to SEQ ID NO: 8 replaced or deleted without substantially affecting binding capacity, and (ii) has an activity of no more than 0.25% of thrombin.

21. A method according to claim 20, wherein at least one amino acid selected from the group consisting of Cys-293 and Cys-439 based on the amino acid numbering in prothrombin according to SEQ ID NO: 8 also is replaced or deleted without substantially affecting binding capacity.

22. A method according to claim 20, wherein said amino acid Asp-419 has been replaced with Asn.

* * * * *

UNITED STATES PATENT AND TRADEMARK OFFICE
CERTIFICATE OF CORRECTION

PATENT NO. : 6,086,871
DATED : July 11, 2000
INVENTOR(S) : Bernhard FISCHER, et al.

It is certified that error appears in the above-identified patent and that said Letters Patent is hereby corrected as shown below:

On the title page, item: [30] Foreign Application Priority Data, delete "1005/95" and replace with --1006/95--.

Signed and Sealed this

Eighth Day of May, 2001

Attest:

NICHOLAS P. GODICI

*Attesting Officer*      *Acting Director of the United States Patent and Trademark Office*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
       (A) LENGTH: 81 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "synthetic MCS1"

(xi) SEQUENCE DESCRIPTION: SEQ ID NO:1:

TCGACCATGG ACAAGCTTAT CGATCCCGGG AATTCGGTAC CGTCGACCTG CAGGTGCACG     60

GGCCCAGATC TGACTGACTG A                                              81

(2) INFORMATION FOR SEQ ID NO:2:

(i) SEQUENCE CHARACTERISTICS:
       (A) LENGTH: 81 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "synthetic MCS2"

(xi) SEQUENCE DESCRIPTION: SEQ ID NO:2:

TCGATCAGTC AGTCAGATCT GGGCCCGTGC ACCTGCAGGT CGACGGTACC GAATTCCCGG     60

GATCGATAAG CTTGTCCATG G                                              81

(2) INFORMATION FOR SEQ ID NO:3:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer 2104"

(xi) SEQUENCE DESCRIPTION: SEQ ID NO:3:

TAACTGACGG TCCTTGAGCT CCATGTTGGA AAAGATCTAC ATC                       43

(2) INFORMATION FOR SEQ ID NO:4:

(i) SEQUENCE CHARACTERISTICS:
       (A) LENGTH: 86 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer 2066"

(xi) SEQUENCE DESCRIPTION: SEQ ID NO:4:

GCAGACACAC AGGGTGAATG TAGTCACTGA AGGCAACAGG CTTCTTCAGC TTCATCAGGG     60

CAATATTCCG GTCCAGGTTC TCCCGC                                         86

(2) INFORMATION FOR SEQ ID NO:5:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 2197"

(xi) SEQUENCE DESCRIPTION: SEQ ID NO:5:

CATAAGCCTG AAATCAACTC                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 2198"

(xi) SEQUENCE DESCRIPTION: SEQ ID NO:6:

CTTCGGAGCG TGGAGTCATC                                                    20

(2) INFORMATION FOR SEQ ID NO:7:

(i) SEQUENCE CHARACTERISTICS:
        (A) LENGTH: 1869 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1866

(ix) FEATURE:
        (A) NAME/KEY: mat_peptide
        (B) LOCATION: 130..1866

(ix) FEATURE:
        (A) NAME/KEY: sig_peptide
        (B) LOCATION: 1..129

(xi) SEQUENCE DESCRIPTION: SEQ ID NO:7:
```

| | | | | | | | | | | | | | | | | |
|---|---|---|---|---|---|---|---|---|---|---|---|---|---|---|---|---|
| ATG | GCG | CAC | GTC | CGA | GGC | TTG | CAG | CTG | CCT | GGC | TGC | CTG | GCC | CTG | GCT | 48 |
| Met | Ala | His | Val | Arg | Gly | Leu | Gln | Leu | Pro | Gly | Cys | Leu | Ala | Leu | Ala | |
| -43 | | -40 | | | -35 | | | | -30 | | | | | | | |
| GCC | CTG | TGT | AGC | CTT | GTG | CAC | AGC | CAG | CAT | GTG | TTC | CTG | GCT | CCT | CAG | 96 |
| Ala | Leu | Cys | Ser | Leu | Val | His | Ser | Gln | His | Val | Phe | Leu | Ala | Pro | Gln | |
| | -25 | | | | | -20 | | | | | -15 | | | | | |
| CAA | GCA | CGG | TCG | CTG | CTC | CAG | CGG | GTC | CGG | CGA | GCC | AAC | ACC | TTC | TTG | 144 |
| Gln | Ala | Arg | Ser | Leu | Leu | Gln | Arg | Val | Arg | Arg | Ala | Asn | Thr | Phe | Leu | |
| | -10 | | | | | -5 | | | | | 1 | | | | 5 | |
| GAG | GAG | GTG | CGC | AAG | GGC | AAC | CTA | GAG | CGA | GAG | TGC | GTG | GAG | GAG | ACG | 192 |
| Glu | Glu | Val | Arg | Lys | Gly | Asn | Leu | Glu | Arg | Glu | Cys | Val | Glu | Glu | Thr | |
| | | | 10 | | | | | 15 | | | | | 20 | | | |
| TGC | AGC | TAC | GAG | GAG | GCC | TTC | GAG | GCT | CTG | GAG | TCC | TCC | ACG | GCT | ACG | 240 |
| Cys | Ser | Tyr | Glu | Glu | Ala | Phe | Glu | Ala | Leu | Glu | Ser | Ser | Thr | Ala | Thr | |
| | | 25 | | | | | 30 | | | | | 35 | | | | |
| GAT | GTG | TTC | TGG | GCC | AAG | TAC | ACA | GCT | TGT | GAG | ACA | GCG | AGG | ACG | CCT | 288 |
| Asp | Val | Phe | Trp | Ala | Lys | Tyr | Thr | Ala | Cys | Glu | Thr | Ala | Arg | Thr | Pro | |
| | | 40 | | | | | 45 | | | | | 50 | | | | |

```
CGA GAT AAG CTT GCT GCA TGT CTG GAA GGT AAC TGT GCT GAG GGT CTG        336
Arg Asp Lys Leu Ala Ala Cys Leu Glu Gly Asn Cys Ala Glu Gly Leu
 55                  60                  65

GGT ACG AAC TAC CGA GGG CAT GTG AAC ATC ACC CGG TCA GGC ATT GAG        384
Gly Thr Asn Tyr Arg Gly His Val Asn Ile Thr Arg Ser Gly Ile Glu
 70                  75                  80                  85

TGC CAG CCA TGG AGG AGT CGC TAC CCA CAT AAG CCT GAA ATC AAC TCC        432
Cys Gln Pro Trp Arg Ser Arg Tyr Pro His Lys Pro Glu Ile Asn Ser
                 90                  95                 100

ACT ACC CAT CCT GGG GCC GAC CTA CAG GAG AAT TTC TGC CGC AAC CCC        480
Thr Thr His Pro Gly Ala Asp Leu Gln Glu Asn Phe Cys Arg Asn Pro
            105                 110                 115

GAC AGC AGC ACC ATG GGA CCC TGG TGC TAC ACT ACA GAC CCC ACC GTG        528
Asp Ser Ser Thr Met Gly Pro Trp Cys Tyr Thr Thr Asp Pro Thr Val
            120                 125                 130

AGG AGG CAG GAA TGC AGC ATC CCT GTC TGT GGC CAG GAT CAA GTC ACT        576
Arg Arg Gln Glu Cys Ser Ile Pro Val Cys Gly Gln Asp Gln Val Thr
            135                 140                 145

GTA GCG ATG ACT CCA CGC TCC GAA GGC TCC AGT GTG AAT CTG TCA CCT        624
Val Ala Met Thr Pro Arg Ser Glu Gly Ser Ser Val Asn Leu Ser Pro
150                 155                 160                 165

CCA TTG GAG CAG TGT GTC CCT GAT CGG GGG CAG CAG TAC CAG GGG CGC        672
Pro Leu Glu Gln Cys Val Pro Asp Arg Gly Gln Gln Tyr Gln Gly Arg
                170                 175                 180

CTG GCG GTG ACC ACA CAT GGG CTC CCC TGC CTG GCC TGG GCC AGC GCA        720
Leu Ala Val Thr Thr His Gly Leu Pro Cys Leu Ala Trp Ala Ser Ala
                185                 190                 195

CAG GCC AAG GCC CTG AGC AAG CAC CAG GAC TTC AAC TCA GCT GTG CAG        768
Gln Ala Lys Ala Leu Ser Lys His Gln Asp Phe Asn Ser Ala Val Gln
                200                 205                 210

CTG GTG GAG AAC TTC TGC CGC AAC CCA GAC GGG GAT GAG GAG GGC GTG        816
Leu Val Glu Asn Phe Cys Arg Asn Pro Asp Gly Asp Glu Glu Gly Val
215                 220                 225

TGG TGC TAT GTG GCC GGG AAG CCT GGC GAC TTT GGG TAC TGC GAC CTC        864
Trp Cys Tyr Val Ala Gly Lys Pro Gly Asp Phe Gly Tyr Cys Asp Leu
230                 235                 240                 245

AAC TAT TGT GAG GAG GCC GTG GAG GAG GAG ACA GGA GAT GGG CTG GAT        912
Asn Tyr Cys Glu Glu Ala Val Glu Glu Glu Thr Gly Asp Gly Leu Asp
                250                 255                 260

GAG GAC TCA GAC AGG GCC ATC GAA GGG CGT ACC GCC ACA AGT GAG TAC        960
Glu Asp Ser Asp Arg Ala Ile Glu Gly Arg Thr Ala Thr Ser Glu Tyr
            265                 270                 275

CAG ACT TTC TTC AAT CCG AGG ACC TTT GGC TCG GGA GAG GCA GAC TGT       1008
Gln Thr Phe Phe Asn Pro Arg Thr Phe Gly Ser Gly Glu Ala Asp Cys
            280                 285                 290

GGG CTG CGA CCT CTG TTC GAG AAG AAG TCG CTG GAG GAC AAA ACC GAA       1056
Gly Leu Arg Pro Leu Phe Glu Lys Lys Ser Leu Glu Asp Lys Thr Glu
            295                 300                 305

AGA GAG CTC CTG GAA TCC TAC ATC GAC GGG CGC ATT GTG GAG GGC TCG       1104
Arg Glu Leu Leu Glu Ser Tyr Ile Asp Gly Arg Ile Val Glu Gly Ser
310                 315                 320                 325

GAT GCA GAG ATC GGC ATG TCA CCT TGG CAG GTG ATG CTT TTC CGG AAG       1152
Asp Ala Glu Ile Gly Met Ser Pro Trp Gln Val Met Leu Phe Arg Lys
                330                 335                 340

AGT CCC CAG GAG CTG CTG TGT GGG GCC AGC CTC ATC AGT GAC CGC TGG       1200
Ser Pro Gln Glu Leu Leu Cys Gly Ala Ser Leu Ile Ser Asp Arg Trp
            345                 350                 355

GTC CTC ACC GCC GCC CAC TGC CTC CTG TAC CCG CCC TGG GAC AAG AAC       1248
Val Leu Thr Ala Ala His Cys Leu Leu Tyr Pro Pro Trp Asp Lys Asn
            360                 365                 370
```

```
TTC ACC GAG AAT GAC CTT CTG GTG CGC ATT GGC AAG CAC TCC CGC ACC      1296
Phe Thr Glu Asn Asp Leu Leu Val Arg Ile Gly Lys His Ser Arg Thr
    375                 380                 385

AGG TAC GAG CGA AAC ATT GAA AAG ATA TCC ATG TTG GAA AAG ATC TAC      1344
Arg Tyr Glu Arg Asn Ile Glu Lys Ile Ser Met Leu Glu Lys Ile Tyr
390                 395                 400                 405

ATC CAC CCC AGG TAC AAC TGG CGG GAG AAC CTG GAC CGG GAC ATT GCC      1392
Ile His Pro Arg Tyr Asn Trp Arg Glu Asn Leu Asp Arg Asp Ile Ala
                410                 415                 420

CTG ATG AAG CTG AAG AAG CCT GTT GCC TTC AGT GAC TAC ATT CAC CCT      1440
Leu Met Lys Leu Lys Lys Pro Val Ala Phe Ser Asp Tyr Ile His Pro
            425                 430                 435

GTG TGT CTG CCC GAC AGG GAG ACG GCA GCC AGC TTG CTC CAG GCT GGA      1488
Val Cys Leu Pro Asp Arg Glu Thr Ala Ala Ser Leu Leu Gln Ala Gly
        440                 445                 450

TAC AAG GGG CGG GTG ACA GGC TGG GGC AAC CTG AAG GAG ACG TGG ACA      1536
Tyr Lys Gly Arg Val Thr Gly Trp Gly Asn Leu Lys Glu Thr Trp Thr
    455                 460                 465

GCC AAC GTT GGT AAG GGG CAG CCC AGT GTC CTG CAG GTG GTG AAC CTG      1584
Ala Asn Val Gly Lys Gly Gln Pro Ser Val Leu Gln Val Val Asn Leu
470                 475                 480                 485

CCC ATT GTG GAG CGG CCG GTC TGC AAG GAC TCC ACC CGG ATC CGC ATC      1632
Pro Ile Val Glu Arg Pro Val Cys Lys Asp Ser Thr Arg Ile Arg Ile
                490                 495                 500

ACT GAC AAC ATG TTC TGT GCT GGT TAC AAG CCT GAT GAA GGG AAA CGA      1680
Thr Asp Asn Met Phe Cys Ala Gly Tyr Lys Pro Asp Glu Gly Lys Arg
            505                 510                 515

GGG GAT GCC TGT GAA GGT GAC AGT GGG GGA CCC TTT GTC ATG AAG AGC      1728
Gly Asp Ala Cys Glu Gly Asp Ser Gly Gly Pro Phe Val Met Lys Ser
        520                 525                 530

CCC TTT AAC AAC CGC TGG TAT CAA ATG GGC ATC GTC TCA TGG GGT GAA      1776
Pro Phe Asn Asn Arg Trp Tyr Gln Met Gly Ile Val Ser Trp Gly Glu
    535                 540                 545

GGC TGT GAC CGG GAT GGG AAA TAT GGC TTC TAC ACA CAT GTG TTC CGC      1824
Gly Cys Asp Arg Asp Gly Lys Tyr Gly Phe Tyr Thr His Val Phe Arg
550                 555                 560                 565

CTG AAG AAG TGG ATA CAG AAG GTC ATT GAT CAG TTT GGA GAG              1866
Leu Lys Lys Trp Ile Gln Lys Val Ile Asp Gln Phe Gly Glu
                570                 575

TAG                                                                   1869

(2) INFORMATION FOR SEQ ID NO:8:

(i) SEQUENCE CHARACTERISTICS:
        (A) LENGTH: 622 amino acids
        (B) TYPE: amino acid
        (D) TOPOLOGY: linear (ii) MOLECULE TYPE: protein (xi) SEQUENCE DESCRIPTION: SEQ ID NO:8:

Met Ala His Val Arg Gly Leu Gln Leu Pro Gly Cys Leu Ala Leu Ala
-43             -40                 -35                 -30

Ala Leu Cys Ser Leu Val His Ser Gln His Val Phe Leu Ala Pro Gln
        -25                 -20                 -15

Gln Ala Arg Ser Leu Leu Gln Arg Val Arg Arg Ala Asn Thr Phe Leu
    -10                 -5                   1                  5

Glu Glu Val Arg Lys Gly Asn Leu Glu Arg Glu Cys Val Glu Glu Thr
                10                  15                  20
```

-continued

```
Cys Ser Tyr Glu Glu Ala Phe Glu Ala Leu Glu Ser Ser Thr Ala Thr
             25                  30                  35

Asp Val Phe Trp Ala Lys Tyr Thr Ala Cys Glu Thr Ala Arg Thr Pro
         40                  45                  50

Arg Asp Lys Leu Ala Ala Cys Leu Glu Gly Asn Cys Ala Glu Gly Leu
         55                  60                  65

Gly Thr Asn Tyr Arg Gly His Val Asn Ile Thr Arg Ser Gly Ile Glu
 70                  75                  80                  85

Cys Gln Pro Trp Arg Ser Arg Tyr Pro His Lys Pro Glu Ile Asn Ser
                 90                  95                 100

Thr Thr His Pro Gly Ala Asp Leu Gln Glu Asn Phe Cys Arg Asn Pro
                105                 110                 115

Asp Ser Ser Thr Met Gly Pro Trp Cys Tyr Thr Thr Asp Pro Thr Val
         120                 125                 130

Arg Arg Gln Glu Cys Ser Ile Pro Val Cys Gly Gln Asp Gln Val Thr
         135                 140                 145

Val Ala Met Thr Pro Arg Ser Glu Gly Ser Ser Val Asn Leu Ser Pro
150                 155                 160                 165

Pro Leu Glu Gln Cys Val Pro Asp Arg Gly Gln Gln Tyr Gln Gly Arg
                170                 175                 180

Leu Ala Val Thr Thr His Gly Leu Pro Cys Leu Ala Trp Ala Ser Ala
                185                 190                 195

Gln Ala Lys Ala Leu Ser Lys His Gln Asp Phe Asn Ser Ala Val Gln
                200                 205                 210

Leu Val Glu Asn Phe Cys Arg Asn Pro Asp Gly Asp Glu Glu Gly Val
                215                 220                 225

Trp Cys Tyr Val Ala Gly Lys Pro Gly Asp Phe Gly Tyr Cys Asp Leu
230                 235                 240                 245

Asn Tyr Cys Glu Glu Ala Val Glu Glu Thr Gly Asp Gly Leu Asp
                250                 255                 260

Glu Asp Ser Asp Arg Ala Ile Glu Gly Arg Thr Ala Thr Ser Glu Tyr
                265                 270                 275

Gln Thr Phe Phe Asn Pro Arg Thr Phe Gly Ser Gly Glu Ala Asp Cys
                280                 285                 290

Gly Leu Arg Pro Leu Phe Glu Lys Lys Ser Leu Glu Asp Lys Thr Glu
295                 300                 305

Arg Glu Leu Leu Glu Ser Tyr Ile Asp Gly Arg Ile Val Glu Gly Ser
310                 315                 320                 325

Asp Ala Glu Ile Gly Met Ser Pro Trp Gln Val Met Leu Phe Arg Lys
                330                 335                 340

Ser Pro Gln Glu Leu Leu Cys Gly Ala Ser Leu Ile Ser Asp Arg Trp
                345                 350                 355

Val Leu Thr Ala Ala His Cys Leu Leu Tyr Pro Pro Trp Asp Lys Asn
                360                 365                 370

Phe Thr Glu Asn Asp Leu Leu Val Arg Ile Gly Lys His Ser Arg Thr
375                 380                 385

Arg Tyr Glu Arg Asn Ile Glu Lys Ile Ser Met Leu Glu Lys Ile Tyr
390                 395                 400                 405

Ile His Pro Arg Tyr Asn Trp Arg Glu Asn Leu Asp Arg Asp Ile Ala
                410                 415                 420

Leu Met Lys Leu Lys Lys Pro Val Ala Phe Ser Asp Tyr Ile His Pro
                425                 430                 435

Val Cys Leu Pro Asp Arg Glu Thr Ala Ala Ser Leu Leu Gln Ala Gly
```

```
                        440                 445                 450
Tyr Lys Gly Arg Val Thr Gly Trp Gly Asn Leu Lys Glu Thr Trp Thr
                455                 460                 465
Ala Asn Val Gly Lys Gly Gln Pro Ser Val Leu Gln Val Val Asn Leu
470                 475                 480                 485
Pro Ile Val Glu Arg Pro Val Cys Lys Asp Ser Thr Arg Ile Arg Ile
                490                 495                 500
Thr Asp Asn Met Phe Cys Ala Gly Tyr Lys Pro Asp Glu Gly Lys Arg
                505                 510                 515
Gly Asp Ala Cys Glu Gly Asp Ser Gly Gly Pro Phe Val Met Lys Ser
                520                 525                 530
Pro Phe Asn Asn Arg Trp Tyr Gln Met Gly Ile Val Ser Trp Gly Glu
535                 540                 545
Gly Cys Asp Arg Asp Gly Lys Tyr Gly Phe Tyr Thr His Val Phe Arg
550                 555                 560                 565
Leu Lys Lys Trp Ile Gln Lys Val Ile Asp Gln Phe Gly Glu
                570                 575
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Thr Ala Thr Ser Glu Tyr Gln Thr Phe Phe Asn Pro Arg Thr Phe
1               5                   10                  15
```

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Ile Val Glu Ser Asp Glu Ile Gly Met Ser Pro Trp Gln
1               5                   10
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Ile Val Glu Ser Asp Ala Glu Ile
1               5
```

(2) INFORMATION FOR SEQ ID NO:12:

(i) SEQUENCE CHARACTERISTICS:
        (A) LENGTH: 28 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

TAACTGACGG TCCTTGAGCT CCATGTTG                                28

(2) INFORMATION FOR SEQ ID NO:13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 2..28

(xi) SEQUENCE DESCRIPTION: SEQ ID NO:13:

G CGA AAC ATT GAA AAG ATC TCC ATG TTG                          28
  Arg Asn Ile Glu Lys Ile Ser Met Leu
   1               5

(2) INFORMATION FOR SEQ ID NO:14:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:14:

Arg Asn Ile Glu Lys Ile Ser Met Leu
 1               5

(2) INFORMATION FOR SEQ ID NO:15:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 2..28

(xi) SEQUENCE DESCRIPTION: SEQ ID NO:15:

G CGA AAC ATT GAA AAG ATA TCC ATG TTG                          28
  Arg Asn Ile Glu Lys Ile Ser Met Leu
   1               5

(2) INFORMATION FOR SEQ ID NO:16:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:16:

```
Arg Asn Ile Glu Lys Ile Ser Met Leu
 1               5
```

(2) INFORMATION FOR SEQ ID NO:17:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..15, 17..49)

(xi) SEQUENCE DESCRIPTION: SEQ ID NO:17:

```
GAA AGG ATC TAC ATC G CGG GAG AAC CTG GAC CGG AAT ATT GCC CTG     46
Glu Arg Ile Tyr Ile   Arg Glu Asn Leu Asp Arg Asn Ile Ala Leu
 1               5                  10                  15

ATG                                                                49
Met
```

(2) INFORMATION FOR SEQ ID NO:18:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:18:

```
Glu Arg Ile Tyr Ile Arg Glu Asn Leu Asp Arg Asn Ile Ala Leu Met
 1               5                  10                  15
```

(2) INFORMATION FOR SEQ ID NO:19:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..15, 17..49)

(xi) SEQUENCE DESCRIPTION: SEQ ID NO:19:

```
GAA AAG ATC TAC ATC G CGG GAG AAC CTG GAC CGG GAC ATT GCC CTG     46
Glu Lys Ile Tyr Ile   Arg Glu Asn Leu Asp Arg Asp Ile Ala Leu
 1               5                  10                  15

ATG                                                                49
Met
```

(2) INFORMATION FOR SEQ ID NO:20:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:20:

Glu Lys Ile Tyr Ile Arg Glu Asn Leu Asp Arg Asp Ile Ala Leu Met

-continued

```
  1               5              10              15
```

(2) INFORMATION FOR SEQ ID NO:21:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..51

(xi) SEQUENCE DESCRIPTION: SEQ ID NO:21:

```
AAG CTG AAG AAG CCT GTT GCC TTC AGT GAC TAC ATT CAC CCT GTG TGT      48
Lys Leu Lys Lys Pro Val Ala Phe Ser Asp Tyr Ile His Pro Val Cys
  1               5                  10                  15

CTG                                                                  51
Leu
```

(2) INFORMATION FOR SEQ ID NO:22:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:22:

```
Lys Leu Lys Lys Pro Val Ala Phe Ser Asp Tyr Ile His Pro Val Cys
  1               5                  10                  15

Leu
```